United States Patent
Albertsen et al.

(10) Patent No.: US 6,956,118 B2
(45) Date of Patent: Oct. 18, 2005

(54) PROMOTER SEQUENCES PROVIDING MALE TISSUE-PREFERRED EXPRESSION IN PLANTS

(75) Inventors: Marc C. Albertsen, Grimes, IA (US); Tim Fox, Des Moines, IA (US); Gary Huffman, Des Moines, IA (US); Mary Trimnell, West Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 48 days.

(21) Appl. No.: 10/058,566

(22) Filed: Jan. 28, 2002

(65) Prior Publication Data

US 2002/0183274 A1 Dec. 5, 2002

Related U.S. Application Data

(60) Provisional application No. 60/267,527, filed on Feb. 8, 2001.

(51) Int. Cl.[7] .............................................. C12N 15/11

(52) U.S. Cl. ...................................................... 536/24.1

(58) Field of Search ........................ 536/24.1; 800/287, 800/290; 435/320.1, 419

(56) References Cited

U.S. PATENT DOCUMENTS 5,859,341 A * 1/1999 Albertsen et al. ........... 800/271
5,929,307 A * 7/1999 Hodges et al. .............. 800/303
6,005,167 A * 12/1999 Van Tunen et al. .......... 800/295

FOREIGN PATENT DOCUMENTS

WO  WO 9328142  9/1993

OTHER PUBLICATIONS

Kim et al, 1994, Plant Mol. Biol. 24:105–117.*
Benfrey et al, 1990, Science 250:959–966.*
Chen et al, 2000, Sex. Plant Reprod. 13:85–94.*
Eyal et al, 1995, Plant Cell 7:373–384.*
Donald et al, 1990 EMBO J. 9:1717–1726.*
Saslowsky et al. "An allelic series for the chalcone synthase locus in *Arabidopsis*" *Gene* (2000) 255 No. 2 127–138.
Pollak et al. "Conditional Male Fertility in Maize" *Sexual Plant Reproduction* (1994) 8 No. 4, 231–241.
Fox et al. "Zea mays dihydro–flavanoid reductase–like protein (ms*–bs7) mRNA" *EMBL* (May 15, 2001) database accession no. AF366295.
Fox et al. "Zea mays dihydro–flavanoid reductase–like protein (ms*–bs7) gene, promoter sequence" *EMBL* (May 15, 2001) database accession No. AF366294.
Walbot, V. "Maize ESTs from various cDNA libraries sequenced at Stanford University" *EMBL* (Mar. 15, 2000) database accession No. AW566168.
Zhuang et al. "Differential expression of a putative dihydrofavonol reductase gene in rice" *EMBL* (Apr. 12, 1999 and Jul. 8, 1999) databasse accession No. AF134807.
Zhuang et al. "Differential expression of a putative dihydrofavonol reductase gene in rice" *Plant Gene Register* (Aug. 1999) PGR 99–074 online and Accession No. AF134807.
Budar, F. and Pelletier, G. "Male sterility in plants: occurrence,determinism, significance and use" *Comptes Redus des Séance de L'academie des Sciences* (2001) 324 No. 6 543–550.

* cited by examiner

*Primary Examiner*—Anne Kubelik
(74) *Attorney, Agent, or Firm*—Patricia A. Sweeney

(57) ABSTRACT

Promoter sequences and their essential regions are identified which provide for male tissue-preferred expression. The nucleotide sequences are useful in mediating male fertility in plants.

2 Claims, 18 Drawing Sheets

FIGURE 4

```
     GGTGACCTCAAGCAAGGGCAAGGTATGCGTAACCGGGGCCTCAGGCTTTGTTGCCTCTTG
  1  ---------+---------+---------+---------+---------+---------+  60
     CCACTGGAGTTCGTTCCCGTTCCATACGCATTGGCCCCGGAGTCCGAAACAACGGAGAAC b     V  T  S  S  K  G  K  V  C  V  T  G  A  S  G  F  V  A  S  W  -

XhoI
                          |
     GCTTATCAAACGGCTCCTCGAGTCTGGATATCATGTGGTAGGGACTGTCAGGGACCCAGG
 61  ---------+---------+---------+---------+---------+---------+ 120
     CGAATAGTTTGCCGAGGAGCTCAGACCTATAGTACACCATCCCTGACAGTCCCTGGGTCC b     L  I  K  R  L  L  E  S  G  Y  H  V  V  G  T  V  R  D  P  G  -

AAATCACCAAAAAACAGCCCACCTTTGGAAATTACCTGGCGCTAAAGAGAGGCTGCAAAT
121  ---------+---------+---------+---------+---------+---------+ 180
     TTTAGTGGTTTTTTGTCGGGTGGAAACCTTTAATGGACCGCGATTTCTCTCCGACGTTTA b     N  H  Q  K  T  A  H  L  W  K  L  P  G  A  K  E  R  L  Q  I  -

CGTGCGAGCTAATCTGTTGGAAGAAGGGAGCTTCGACAGCGCCGTGATGGCCTGTGAGGG
181  ---------+---------+---------+---------+---------+---------+ 240
     GCACGCTCGATTAGACAACCTTCTTCCCTCGAAGCTGTCGCGGCACTACCGGACACTCCC b     V  R  A  N  L  L  E  E  G  S  F  D  S  A  V  M  A  C  E  G  -

TGTATTCCACACTGCATCCCCCGTCCTCGCTAAACCCGACTCTACTAGCAAGGAGGACAC
241  ---------+---------+---------+---------+---------+---------+ 300
     ACATAAGGTGTGACGTAGGGGGCAGGAGCGATTTGGGCTGAGATGATCGTTCCTCCTGTG b     V  F  H  T  A  S  P  V  L  A  K  P  D  S  T  S  K  E  D  T  -

GCTCGTCCCTGCGGTGAACGGTACTCTGAACGTGCTGAGATCGTGCAAGAAGAACCCCTT
301  ---------+---------+---------+---------+---------+---------+ 360
     CGAGCAGGGACGCCACTTGCCATGAGACTTGCACGACTCTAGCACGTTCTTCTTGGGGAA b     L  V  P  A  V  N  G  T  L  N  V  L  R  S  C  K  K  N  P  F  -

CCTGAAAAGGGTCGTCCTTACGTCTTCGTCGTCTGCGGTGAGGATCAGGGACGACGGTGG
361  ---------+---------+---------+---------+---------+---------+ 420
     GGACTTTTCCCAGCAGGAATGCAGAAGCAGCAGACGCCACTCCTAGTCCCTGCTGCCACC b     L  K  R  V  V  L  T  S  S  S  S  A  V  R  I  R  D  D  G  -

CCAGTCCAGTAACATCTCGCTGGACGAAACGACATGGAGCTCCGTGCCACTCTGCGAGAA
421  ---------+---------+---------+---------+---------+---------+ 480
     GGTCAGGTCATTGTAGAGCGACCTGCTTTGCTGTACCTCGAGGCACGGTGAGACGCTCTT b     Q  S  S  N  I  S  L  D  E  T  T  W  S  S  V  P  L  C  E  K  -
```

FIGURE 4B

```
      GATGCATCTATGGTATGCCCTAGCCAAGGTATTTGCAGAGAAAGCGGCGTGGGAGTTCGC
  481 ---------+---------+---------+---------+---------+---------+ 540
      CTACGTAGATACCATACGGGATCGGTTCCATAAACGTCTCTTTCGCCGCACCCTCAAGCG b       M  H  L  W  Y  A  L  A  K  V  F  A  E  K  A  A  W  E  F  A  -

CAAGGAGAACGGCATCGACCTTGTGACTGTCCTCCCGTCGTTCGTGATCGGGCCCAGTTT
  541 ---------+---------+---------+---------+---------+---------+ 600
      GTTCCTCTTGCCGTAGCTGGAACACTGACAGGAGGGCAGCAAGCACTAGCCCGGGTCAAA b       K  E  N  G  I  D  L  V  T  V  L  P  S  F  V  I  G  P  S  L  -

GTCCCACGAGCTATGCGTTACCGCTTCAGACGTCCTAGGCCTATTCCAAGGCGACACGGC
  601 ---------+---------+---------+---------+---------+---------+ 660
      CAGGGTGCTCGATACGCAATGGCGAAGTCTGCAGGATCCGGATAAGGTTCCGCTGTGCCG b       S  H  E  L  C  V  T  A  S  D  V  L  G  L  F  Q  G  D  T  A  -

AAGGTTCAGCTCGTACGGAAGAATGGGGTACGTCCACATCGACGACGTTGCGAGCAGCCA
  661 ---------+---------+---------+---------+---------+---------+ 720
      TTCCAAGTCGAGCATGCCTTCTTACCCCATGCAGGTGTAGCTGCTGCAACGCTCGTCGGT b       R  F  S  S  Y  G  R  M  G  Y  V  H  I  D  D  V  A  S  S  H  -

CATCCTGGTGTACGAGGTCCCCCAGGCCGCCGGGAGGTACCTGTGCAGCTCAGTGGTGCT
  721 ---------+---------+---------+---------+---------+---------+ 780
      GTAGGACCACATGCTCCAGGGGGTCCGGCGGCCCTCCATGGACACGTCGAGTCACCACGA b       I  L  V  Y  E  V  P  Q  A  A  G  R  Y  L  C  S  S  V  V  L  -

GGACAACGACGAGCTGGTCTCCTCGCTCGCGAAACGCTACCCGATATTCCCCATACCCCG
  781 ---------+---------+---------+---------+---------+---------+ 840
      CCTGTTGCTGCTCGACCAGAGGAGCGAGCGCTTTGCGATGGGCTATAAGGGGTATGGGGC b       D  N  D  E  L  V  S  S  L  A  K  R  Y  P  I  F  P  I  P  R  -

GAGGCTGAACAGCCCCTACGGCAAGCAGTCGTACCAGCTGAACACGTCGAAGCTGCAGGG
  841 ---------+---------+---------+---------+---------+---------+ 900
      CTCCGACTTGTCGGGGATGCCGTTCGTCAGCATGGTCGACTTGTGCAGCTTCGACGTCCC b       R  L  N  S  P  Y  G  K  Q  S  Y  Q  L  N  T  S  K  L  Q  G  -

GCTGGGCTTCAAGTTCAGAGGGGTGCAGGAGATGTTCGACGACTGCGTGCAGTCGCTCAA
  901 ---------+---------+---------+---------+---------+---------+ 960
      CGACCCGAAGTTCAAGTCTCCCCACGTCCTCTACAAGCTGCTGACGCACGTCAGCGAGTT b       L  G  F  K  F  R  G  V  Q  E  M  F  D  D  C  V  Q  S  L  K  -

AGACCAGGGCCACCTGCTGGAGTGCCCCCTGTGAACTGCGATGGGGGTGCCTCCTGTGAA
  961 ---------+---------+---------+---------+---------+---------+ 1020
      TCTGGTCCCGGTGGACGACCTCACGGGGGACACTTGACGCTACCCCCACGGAGGACACTT b       D  Q  G  H  L  L  E  C  P  L  *
```

FIGURE 4C

```
     CGCCCGTTTTTTTTTTTCTTCAATAATTCCACGTCATGTCACGGTGTCCTCGCGAGACT
1021 ---------+---------+---------+---------+---------+---------+ 1080
     GCGGGCAAAAAAAAAAAGAAGTTATTAAGGTGCAGTACAGTGCCACAGGAGCGCGTCTGA

GCTACTGTCAGGTGTCAGGGCGTCATAGCTCACGGGCTCTACGGCTACATGAATAAAATG
1081 ---------+---------+---------+---------+---------+---------+ 1140
     CGATGACAGTCCACAGTCCCGCAGTATCGAGTGCCCGAGATGCCGATGTACTTATTTTAC

XhoI
                                                           |
     TCACGCTAGCTCGTCATTTGCTTTGCCATTTAAAAAAAAAAAAAAAAAAAACTCGAG
1141 ---------+---------+---------+---------+---------+------- 1197
     AGTGCGATCGAGCAGTAAACGAAACGGTAAATTTTTTTTTTTTTTTTTTTTGAGCTC
```

FIGURE 5

```
   1  GAATTCTCGT CTCGGCGGTC AACTGAACCG TAAACAGTGG AAAGTGGATA
  51  CTCTTTCTCT CTCTGCAATC CGTGCCGTGG AAGCAAATGG CGCAGTCGCC
 101  TACTTATCAC ACCAACTTAT CACCTAGAAA AGCGACGCGT CCTGGATCGA
 151  TTGCAAATCT ACCTCCAACC AACCCAGCTT TGTATCTGCT TACTGTGATC
 201  ACCAAAGTTG TGCTGATACG ATGTGCGATT ATTGCTCTTT CTTCTCTAGA
 251  ATGTTCCTGC CGATGCTTTA TAAGAGAAGG TTGGTCAGCA TCGATCTCTG
 301  CCAGTGTCTA GCTGAGAACA TGGTGACCTC AAGCAAGGGC AAGGTATGCG
 351  TAACCGGGGC CTCAGGCTTT GTTGCCTCTT GGCTTATCAA ACGGCTCCTC
 401  GAGTCTGGAT ATCATGTGGT AGGGACTGTC AGGGACCCAG GTATTTGCGA
 451  AATATCATTA CTATCGTATC AGTCCTCTTT ATTACATTAA TAATTCTTGA
 501  TTACCAATTT TTTCTTTTTT TTTTTTGGTA ACCCACAAGG AAATCACCAA
 551  AAGACAGCCC ACCTTTGGAA ATTACCTGGC GCTAAAGAGA GGCTGCAAAT
 601  CGTGCGAGCT GATCTGTTGG AAGAAGGGAG CTTCGACAGC GCCGTGATGG
 651  CCTGTGAGGG TGTATTCCAC ACTGCATCCC CCGTCCTCGC TAAACCCGAC
 701  TCTACTAGCA AGGCATGCCA TCGCCGCATA TATATATGCA TATCTGGACC
 751  ATGCATCCTA CTGCAGCCTT TTCTATACGG AAGCGCGTTG CATCTACCGT
 801  ACGTGAAGCT AGCTATCTAA GCTAAGCTGT TTTTCATGCA TGCATGGTGC
 851  AGGAGGACAC GCTCGTCCCT GCGGTGAACG GTACTCTGAA CGTGCTGAGA
 901  TCGTGCAAGA AGAACCCGTT CCTGAAAAGG GTCGTCCTTA CGTCTTCGTC
 951  GTCTGCGGTG AGGATCAGGG ACGACGGTGG CCAGTCCAGT AACATCTCGC
1001  TGGACGAAAC GACATGGAGC TCCGTGCCAC TCTGCGAGAA GATGCATGTG
1051  AGATACTACT GAACAGTGTC TACTCTCTCT CTCTCTGTCA TCGATCTCAA
1101  ACCGTGATCT GAAAACACG CATGCGCGCA CACGTTGCCG TCGTCGTCCC
1151  TTTTGTTGTT CACCCGAAGC TATGGTATGC CCTAGCCAAG GTATTTGCAG
1201  AGAAAGCGGC GTGGGAGTTC GCCAAGGAGA ACGGCATCGA CCTTGTGACT
1251  GTCCTCCCGT CGTTCGTGAT CGGGCCCAGT TTGTCCCACG AACTATGCGT
1301  TACCGCTTCA GACGTCCTAG GCCTATTCCA AGGTATTCAT CTCAATCATT
```

FIGURE 5B

```
1351    CGTACGTGTT CTGGTTTTCG TATGTTAAAT AGATGACTGG AAACAAGAGG

1401    TATACATATA TATACTCTCT GTTCCTCCTC CCCCCCCCCC CCCACCCCCA

1451    GGCGACACGG CAAGGTTCAG CTCGTACGGA AGAATGGGGT ACGTCCACAT

1501    CGACGACGTT GCGAGCAGCC ACATCCTGGT GTACGAGGCC CCCCAGGCCG

1551    CCGGGAGGTA CCTGTGCAGC TCAGTGGTGC TGGACAACGA CGAGCTGGTC

1601    TCCTCGCTCG CGAAACGCTA CCCGATATTC CCCATACCCC GGAGGTCAGT

1651    CGTCGTCGCG TCGTCTGGAT GTGCGTGCCA TTTTAAGATC TCTGAACGGG

1701    AGAGCCGTGT GCATGGTCCG TTCTGCTGCA GGCTGAACAG CCCCTACGGC

1751    AAGCAGTCGT ACCAGCTGAA CACGTCGAAG CTGCAGGGGC TGGGCTTCAA

1801    GTTCAGAGGG GTGCAGGAgA TGTTCGACgA CTGCGTACAG TCGCTCAAAG

1851    ACCAGGGACA CCTGCTGGAG TGCCCCTGT GAACTGCGAT GGGGTGCCTC

1901    CGCCTGTGAA CGCGCCGGTT GGGTTGCGTC CCGAACCCGC TGTTAATTCG

1951    TTTTTTTTTC TTCAATAATT CCACGTCATG TCACGGTGTC CTCGCGCAgA

2001    CTGCTACTGT CAGGGCGTCA TAGCTCACGG GCTCTCCGGC TACATGAATA

2051    AAAATGTCAC GCTCGTCATT TGCTTTGCCT TTTTTTTTGG GTTCGTTCTG

2101    CGAaCTTCCG TTCGCTCTGT GTACTTGTGG CTGCCGGTCg CCTTGTCgGT

2151    GTGGCGACTG ATGATGGTGA TCGCAGGCAG GCACCGGTGT GTGCGTGCGA

2201    TCAACCGAAC GCCATGTGGC GGTTTGGATG GACGAATGGC TCCACCATCG

2251    ATCTGAGTCA TTCGGATTTT GAACCGCTGA TTTGTCCACT GGACGGCACT

2301    AGCATCAAGA TTCAGTCTCA AATCCCAAAT TCCTCAACGC AAAGCCACAA

2351    AGAGAGAATG AATGTACAGT GTTTCAAGCC ACAGCTCAcT AGcTCAAAAG

2401    TAGTGAGCAT GcACACCTGT ATTTACATGC ATGCATGTAC ACCCCCACCC

2451    CCACTACTTG TACACTTTGT AAACCAACCA ACCAACCAAC CAAGCAAGCA

2501       ATCAAGCAAA CACACAGAGC AAACCGTACG TGGCTGCCGC C
```

Figure 6

```
301 CCAGTGTCTAGCTGAGAACATGGTGACCTCAAGCAAGGGCAAGGTATGCG 350
                             ||||||||||||||||||||||||||||||
  1 .....................GGTGACCTCAAGCAAGGGCAAGGTATGCG  29

351 TAACCGGGGCCTCAGGCTTTGTTGCCTCTTGGCTTATCAAACGGCTCCTC 400
    ||||||||||||||||||||||||||||||||||||||||||||||||||
 30 TAACCGGGGCCTCAGGCTTTGTTGCCTCTTGGCTTATCAAACGGCTCCTC  79

401 GAGTCTGGATATCATGTGGTAGGGACTGTCAGGGACCCAGGTATTTGCGA 450
    |||||||||||||||||||||||||||||||||||||
 80 GAGTCTGGATATCATGTGGTAGGGACTGTCAGGGACCC............ 117

501 TTACCAATTTTTTCTTTTTTTTTTTGGTAACCCACAAGGAAATCACCAA 550
                                         |||||||||||||
118 .........................................AGGAAATCACCAA 130

551 AAGACAGCCCACCTTTGGAAATTACCTGGCGCTAAAGAGAGGCTGCAAAT 600
    || |||||||||||||||||||||||||||||||||||||||||||||||
131 AAAACAGCCCACCTTTGGAAATTACCTGGCGCTAAAGAGAGGCTGCAAAT 180

601 CGTGCGAGCTGATCTGTTGGAAGAAGGGAGCTTCGACAGCGCCGTGATGG 650
    |||||||||| |||||||||||||||||||||||||||||||||||||||
181 CGTGCGAGCTAATCTGTTGGAAGAAGGGAGCTTCGACAGCGCCGTGATGG 230

651 CCTGTGAGGGTGTATTCCACACTGCATCCCCCGTCCTCGCTAAACCCGAC 700
    ||||||||||||||||||||||||||||||||||||||||||||||||||
231 CCTGTGAGGGTGTATTCCACACTGCATCCCCCGTCCTCGCTAAACCCGAC 280

701 TCTACTAGCAAGGCATGCCATCGCCGCATATATATATGCATATCTGGACC 750
    ||||||||||
281 TCTACTAGCA........................................ 290

851 AGGAGGACACGCTCGTCCCTGCGGTGAACGGTACTCTGAACGTGCTGAGA 900
    ||||||||||||||||||||||||||||||||||||||||||||||||||
291 AGGAGGACACGCTCGTCCCTGCGGTGAACGGTACTCTGAACGTGCTGAGA 340

901 TCGTGCAAGAAGAACCCGTTCCTGAAAAGGGTCGTCCTTACGTCTTCGTC 950
    |||||||||||||||||| |||||||||||||||||||||||||||||||
341 TCGTGCAAGAAGAACCCCTTCCTGAAAAGGGTCGTCCTTACGTCTTCGTC 390

951 GTCTGCGGTGAGGATCAGGGACGACGGTGGCCAGTCCAGTAACATCTCGC 1000
    ||||||||||||||||||||||||||||||||||||||||||||||||||
391 GTCTGCGGTGAGGATCAGGGACGACGGTGGCCAGTCCAGTAACATCTCGC 440
```

FIGURE 6B

```
1001 TGGACGAAACGACATGGAGCTCCGTGCCACTCTGCGAGAAGATGCATGTG 1050
     ||||||||||||||||||||||||||||||||||||||||||||||
 441 TGGACGAAACGACATGGAGCTCCGTGCCACTCTGCGAGAAGATGCAT... 487

1151 TTTTGTTGTTCACCCGAAGCTATGGTATGCCCTAGCCAAGGTATTTGCAG 1200
                       |||||||||||||||||||||||||||||||
 488 ....................CTATGGTATGCCCTAGCCAAGGTATTTGCAG 518

1201 AGAAAGCGGCGTGGGAGTTCGCCAAGGAGAACGGCATCGACCTTGTGACT 1250
     ||||||||||||||||||||||||||||||||||||||||||||||||||
 519 AGAAAGCGGCGTGGGAGTTCGCCAAGGAGAACGGCATCGACCTTGTGACT 568

1251 GTCCTCCCGTCGTTCGTGATCGGGCCCAGTTTGTCCCACGAACTATGCGT 1300
     ||||||||||||||||||||||||||||||||||||||| |||||||
 569 GTCCTCCCGTCGTTCGTGATCGGGCCCAGTTTGTCCCACGAGCTATGCGT 618

1301 TACCGCTTCAGACGTCCTAGGCCTATTCCAAGGTATTCATCTCAATCATT 1350
     |||||||||||||||||||||||||||||
 619 TACCGCTTCAGACGTCCTAGGCCTATTCCA.................... 648

1401 TATACATATATATACTCTCTGTTCCTCCTCCCCCCCCCCCCCACCCCCA 1450
                                                     |
 649 ................................................A 649

1451 GGCGACACGGCAAGGTTCAGCTCGTACGGAAGAATGGGGTACGTCCACAT 1500
     ||||||||||||||||||||||||||||||||||||||||||||||||||
 650 GGCGACACGGCAAGGTTCAGCTCGTACGGAAGAATGGGGTACGTCCACAT 699

1501 CGACGACGTTGCGAGCAGCCACATCCTGGTGTACGAGGCCCCCAGGCCG 1550
     ||||||||||||||||||||||||||||||||||||||| |||||||||
 700 CGACGACGTTGCGAGCAGCCACATCCTGGTGTACGAGGTCCCCAGGCCG 749

1551 CCGGGAGGTACCTGTGCAGCTCAGTGGTGCTGGACAACGACGAGCTGGTC 1600
     ||||||||||||||||||||||||||||||||||||||||||||||||||
 750 CCGGGAGGTACCTGTGCAGCTCAGTGGTGCTGGACAACGACGAGCTGGTC 799

1601 TCCTCGCTCGCGAAACGCTACCCGATATTCCCCATACCCCGGAGGTCAGT 1650
     |||||||||||||||||||||||||||||||||||||||
 800 TCCTCGCTCGCGAAACGCTACCCGATATTCCCCATACCCCGG........ 841

1701 AGAGCCGTGTGCATGGTCCGTTCTGCTGCAGGCTGAACAGCCCCTACGGC 1750
                                  |||||||||||||||||||||
 842 .............................AGGCTGAACAGCCCCTACGGC 862
```

FIGURE 6C

```
1751 AAGCAGTCGTACCAGCTGAACACGTCGAAGCTGCAGGGGCTGGGCTTCAA 1800
     ||||||||||||||||||||||||||||||||||||||||||||||||||
 863 AAGCAGTCGTACCAGCTGAACACGTCGAAGCTGCAGGGGCTGGGCTTCAA  912

1801 GTTCAGAGGGGTGCAGGAgATGTTCGACgACTGCGTACAGTCGCTCAAAG 1850
     |||||||||||||||||||||||||||||||||||| |||||||||||||
 913 GTTCAGAGGGGTGCAGGAGATGTTCGACGACTGCGTGCAGTCGCTCAAAG  962

1851 ACCAGGGACACCTGCTGGAGTGCCCCTGTGAACTGCGATGGGGTGCCTC 1900
     |||||| |||||||||||||||||||||||||||||||||||  |   |
 963 ACCAGGGCCACCTGCTGGAGTGCCCCTGTGAACTGCGATGGG...GGTGC 1010

1901 CGCCTGTGAACGCGCCGGTTGGGTTGCGTCCCGAACCCGCTGTTAATTCG 1950
     | |||||||||||| |
1011 CTCCTGTGAACGCCC........................GTT 1028

1951 TTTTTTTTTCTTCAATAATTCCACGTCATGTCACGGTGTCCTCGCGCAgA 2000
     ||||||||||||||||||||||||||||||||||||||||||||||||||
1029 TTTTTTTTTCTTCAATAATTCCACGTCATGTCACGGTGTCCTCGCGCAGA 1078

2001 CTGCTAC.......TGTCAGGGCGTCATAGCTCACGGGCTCTCCGGCTAC 2043
     |||||||        |||||||||||||||||||||||||  |||||||
1079 CTGCTACTGTCAGGTGTCAGGGCGTCATAGCTCACGGGCTCTACGGCTAC 1128

2044 ATGAATAAAA...ATGTCACGCTCGTCATTTGCTTTGCCTTTTTTTTGG 2090
     |||||||||    |  ||||||||||||||||||||||||   |||
1129 ATGAATAAAATGTCACGCTAGCTCGTCATTTGCTTTGCCATTTAAAAAA 1178

2091 GTTCGTTCTGCGAaCTTCCGTTCGCTGTGTGTACTTGTGGCTGCCGGTCg 2140
     |
1179 AAAAAAAAAAAAACTCGAG............................... 1197
```

DEVELOPMENTAL GENE EXPRESSION IN MICROSPORO-
GENESIS OF THE MALE FERTILITY GENE BS92-7.
23 HR. EXP

Figure 8

1  GAATTCTCGT CTCGGCGGTC AACTGAACCG TAAACAGTGG AAAGTGGATA

51  CTCTTTCTCT CTCTGCAATC CGTGCCGTGG AAGCAAATGG CGCAGTCGCC

101  TACTTATCAC ACCAACTTAT CACCTAGAAA AGCGACGCGT CCTGGATCGA

151  TTGCAAATCT ACCTCCAACC AACCCAGCTT TGTATCTGCT TACTGTGATC

201  ACCAAAGTTG TGCTGATACG ATGTGCGATT ATTGCTCTTT CTTCTCTAGA

251  ATGTTCCTGC CGATGCTTTA TAAGAGAAGG TTGGTCAGCA TCGATCTCTG

301  CCAGTGTCTA GCTGAGAACA TG

Figure 10

```
  1  CGCGTCCTGG ATCGATTGCA AATCTACCTC CAACCAACCC AGCTTTGTAT

51  CTGCTTACTG TGATCACCAA AGTTGTGCTG ATACGATGTG CGATTATTGC

101  TCTTTCTTCT CTAGAATGTT CCTGCCGATG CTTTATAAGA GAAGGTTGGT

151  CAGCATCGAT CTCTGCCAGT GTCTAGCTGA GAACATG
```

Figure 12

```
                                    V   T   G   A   S   G   F
                                    GTAACCGGGGCTTCAGGCT 50
Sorghum
                                    |||||||||||| |||||||
Maize                               GTAACCGGGGCCTCAGGCT 34
                                    V   T   G   A   S   G   F I   A   S   W   L   I   K   R   L   L   E   S   G   Y   H   V
Sorghum   51 TTATTGCCTCTTGGCTTATCAAACGGCTGCTCGAGTCTGGATATCATGTG 100
             || ||||||||||||||||||||||||||| |||||||||||||||||||
Maize     35 TTGTTGCCTCTTGGCTTATCAAACGGCTCCTCGAGTCTGGATATCATGTG 84
             V   A   S   W   L   I   K   R   L   L   E   S   G   Y   H   V V   G   T   V   R   D   P   G   N   H   Q   K   T   A   H   L   W
Sorghum  101 GTAGGGACTGTCAGAGACCCAGGAAATCACCAAAAAACAGCACACCTTTG 150
             |||||||||||| ||||||||||||||||||||||||||| |||||||
Maize     85 GTAGGGACTGTCAGGGACCCAGGAAATCACCAAAAAACAGCCCACCTTTG 134
             V   G   T   V   R   D   P   G   N   H   Q   K   T   A   H   L   W K   L   P   G   A   K   E   R   L   Q   I   V   R   A   D   L   L
Sorghum  151 GAAATTACCTGGTGCCAAAGAGAGGCTGCAAATTGTGCGAGCTGATCTGT 200
             |||||||||| || |||||||||||||||| |||||||||| ||||||
Maize    135 GAAATTACCTGGCGCTAAAGAGAGGCTGCAAATCGTGCGAGCTAATCTGT 184
             K   L   P   G   A   K   E   R   L   Q   I   V   R   A   N   L   L E   E   G   S   F   D   N   A   V   M   D   C   D   G   V   F
Sorghum  201 TGGAAGAAGGGAGCTTTGACAATGCTGTCATGGACTGTGATGGCGTCTTC 250
             |||||||||||||| |||| || || |||| |||||| || || |||
Maize    185 TGGAAGAAGGGAGCTTCGACAGCGCCGTGATGGCCTGTGAGGGTGTATTC 234
             E   E   G   S   F   D   S   A   V   M   A   C   E   G   V   F H   T   A   S   P   V   L   A   K   S   D   S   S   K   E   E
Sorghum  251 CACACTGCATCCCCTGTGCTCGCTAAATCTGATTCTAGTAGCAAGGAGGA 300
             |||||||||||||| || |||||||| | || |||| |||||||||||
Maize    235 CACACTGCATCCCCCGTCCTCGCTAAACCCGACTCTACTAGCAAGGAGGA 284
             H   T   A   S   P   V   L   A   K   P   D   S   T   S   K   E   E T   L   V   P   A   V   N   G   T   L   N   V   L   R   S   C   K
Sorghum  301 AACGCTTTGTCCAGCAGTAAACGGTACTCTGAATGTGCTAAGATCGTGCA 350
             | ||| || || || |||||||||||||| |||| ||||||||||||
Maize    285 CACGCTCGTCCCTGCGGTGAACGGTACTCTGAACGTGCTGAGATCGTGCA 334
             T   L   V   P   A   V   N   G   T   L   N   V   L   R   S   C   K K   N   P   F   L   K   R   V   V   L   T   S   S   S   A
Sorghum  351 AGAAGAACCCATTTCTGAAAAGGGTTGTTCTTACGTCTTCATCATCTGCA 400
             ||||||||| || ||||||||||| || ||||||||||| || ||||
Maize    335 AGAAGAACCCCTTCCTGAAAAGGGTCGTCCTTACGTCTTCGTCGTCTGCG 384
             K   N   P   F   L   K   R   V   V   L   T   S   S   S   A
```

FIGURE 12B

```
              V  R  I  R  D  D  D  Q        P  N  I  S  L  D  E
Sorghum  401  GTGAGGATTAGGGATGATGATCAGC......CTAATATCTCACTGGATGA  444
              ||||||||  |||||  ||  |  |     |    |||  |||||  |||||  ||
Maize    385  GTGAGGATCAGGGACGACGGTGGCCAGTCCAGTAACATCTCGCTGGACGA  434
              V  R  I  R  D  D  G  G  Q  S  S  N  I  S  L  D  E T  T  W  S  S  V  P  L  C  E  K  M  Q  L  W  Y  A
Sorghum  445  AACAACATGGAGCTCTGTGCCACTCTGTGAAAAGATGCAGCTATGGTATG  494
              |||  |||||||||||||  |||||||||||  ||  ||||||||  ||||||||||
Maize    435  AACGACATGGAGCTCCGTGCCACTCTGCGAAAAGATGCATCTATGGTATG  484
              T  T  W  S  S  V  P  L  C  E  K  M  H  L  W  Y  A L  A  K  V  F  A  E  K  A  A  W  E  F  A  K  E
Sorghum  495  CCCTAGCGAAGGTATTTGCAGAGAAAGCGGCATGGGAATTCGCCAAGGAG  544
              |||||||  |||||||||||||||||||||||||  |||||  ||||||||||||
Maize    485  CCCTAGCCAAGGTATTTGCAGAGAAAGCGGCGTGGGAGTTCGCCAAGGAG  534
              L  A  K  V  F  A  E  K  A  A  W  E  F  A  K  E N  N  I  D  L  V  T  V  L  P  S  F  V  I  G  P  S
Sorghum  545  AACAACATCGACCTTGTGACTGTCCTCCCATCATTTGTGATCGGGCCCAG  594
              |||  ||||||||||||||||||||||||||||||||  ||  ||  ||||||||||||||||
Maize    535  AACGGCATCGACCTTGTGACTGTCCTCCCGTCGTTCGTGATCGGGCCCAG  584
              N  G  I  D  L  V  T  V  L  P  S  F  V  I  G  P  S L  S  H  E  L  C  V  T  A  S  D  V  L  G  L  F  Q
Sorghum  595  TTTATCCCATGAACTATGTGTTACCGCTTCAGATGTCCTAGGCTTATTCC  644
              |||  ||||||  ||  ||||||  ||||||||||||||||  ||||||||||  ||||||
Maize    585  TTTGTCCCACGAGCTATGCGTTACCGCTTCAGACGTCCTAGGCCTATTCC  634
              L  S  H  E  L  C  V  T  A  S  D  V  L  G  L  F  Q G  D  T  A  R  F  S  S  Y  G  R  M  G  Y  V  H
Sorghum  645  AAGGTGACACGGCAAGGTTCAGTTCTTACGGAAGAATGGGATACGTTCAC  694
              ||||  ||||||||||||||||||||  ||  ||||||||||||||||||  |||  |||
Maize    635  AAGGCGACACGGCAAGGTTCAGCTCGTACGGAAGAATGGGGTACGTCCAC  684
              G  D  T  A  R  F  S  S  Y  G  R  M  G  Y  V  H I  D  D  V  A  T  S  H  I  L  V
Sorghum  695  ATCGACGATGTTGCGACCAGCCACATCCTGGTGT  725
              ||||||||  ||||||  ||||||||||||||||||||||||
Maize    685  ATCGACGACGTTGCGAGCAGCCACATCCTGGTGT  718
              I  D  D  V  A  S  S  H  I  L  V
```

PROMOTER SEQUENCES PROVIDING MALE TISSUE-PREFERRED EXPRESSION IN PLANTS

This application claims priority to previously filed and provisional application U.S. Ser. No. 60/267,527, filed Feb. 8, 2001, now abandoned.

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

In *Brassica*, the plant is normally self sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

A reliable method of controlling fertility in plants would offer the opportunity for improved plant breeding. This is especially true for development of maize hybrids, which relies upon some sort of male sterility system and where a female sterility system would reduce production costs.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which has been planted in alternating rows with the male inbred parent. Consequently, providing that there is sufficient isolation from sources of foreign maize pollen, the ears of the female inbred will be fertilized only with pollen from the male inbred. The resulting seed is therefore hybrid and will form hybrid plants.

Environmental variation in plant development can result in plants tasseling after manual detasseling of the female parent is completed. Or, a detasseler might not completely remove the tassel of a female inbred plant. In any event, the result is that the female plant will successfully shed pollen and some female plants will be self-pollinated. This will result in seed of the female inbred being harvested along with the hybrid seed, which is normally produced. Female inbred seed is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives, which further reduce production costs and eliminate self-pollination in the production of hybrid seed.

A reliable system of genetic male sterility would provide advantages. The laborious detasseling process can be avoided in some genotypes by using cytoplasmic male-sterile (CMS) inbreds. In the absence of a fertility restorer gene, plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to insure diversity.

There can be other drawbacks to CMS. One is an historically observed association of a specific variant of CMS with susceptibility to certain crop diseases. This problem has discouraged widespread use of that CMS variant in producing hybrid maize and has had a negative impact on the use of CMS in maize in general.

One type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make use of the system convenient. Patterson also described a genic system of chromosomal translocations which can be effective, but which are complicated. U.S. Pat. Nos. 3,861,709 and 3,710,511.

Many other attempts have been made to improve on these drawbacks. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Mariani, et al. also shows several cytotoxic and antisense systems. See EP 89/401,194. Still other systems use "repressor" genes which inhibit the expression of another gene critical to male sterility. PCT/GB90/00102, published as WO 90/08829.

A still further improvement of this system is one described at U.S. Pat. No. 5,478,369 (incorporated herein by reference) in which a method of imparting controllable male sterility is achieved by silencing a gene native to the plant that is critical for male fertility and replacing the native DNA with the gene critical to male fertility linked to an inducible promoter controlling expression of the gene. The plant is thus constitutively sterile, becoming fertile only when the promoter is induced and its attached male fertility gene is expressed.

As noted, an essential aspect of much of the work underway with male sterility systems is the identification of genes impacting male fertility.

Such a gene can be used in a variety of systems to control male fertility including those described herein. Previously, a male fertility gene has been identified in *Arabidopsis thaliana* and used to produce a male sterile plant. Aarts, et al., "Transposon Tagging of a Male Sterility Gene in *Arabidopsis*", Nature. 363:715–717 (Jun. 24, 1993). U.S. Pat. No. 5,478,369 discloses therein one such gene impacting male fertility. In the present invention the inventors provide novel DNA molecules and the amino acid sequence encoded that are critical to male fertility in plants. The inventors also provide a promoter of the gene and its essential sequences. These can be used in any of the systems where control of fertility is useful, including those described above.

Thus, one object of the invention is to provide a nucleic acid sequence, the expression of which is critical to male fertility in plants.

Another object of the invention is to provide a DNA molecule encoding an amino acid sequence, the expression of which is critical to male fertility in plants.

Yet another object of the invention is to provide a promoter of such nucleotide sequence and its essential sequences.

A further object of the invention is to provide a method of using such DNA molecules to mediate male fertility in plants.

Further objects of the invention will become apparent in the description and claims that follow.

SUMMARY OF THE INVENTION

This invention relates to nucleic acid sequences, and, specifically, DNA molecules and the amino acid encoded by the DNA molecules, which are critical to male fertility. A promoter of the DNA is identified, as well as its essential sequences. It also relates to use of such DNA molecules to mediate fertility in plants.

BRIEF DESCRIPTION OF THE DRAWINGS

FIG. 4 shows the nucleotide and protein sequences of the cDNA of BS92-7 (The cDNA is SEQ ID NO: 1, the protein is SEQ ID NO: 1).

FIG. 5 is the genomic BS92-7 sequence (the nucleotide sequence is also referred to as SEQ ID NO: 3.

FIG. 6 is comparisons of the genomic BS92-7 sequence with the cDNA, (SEQ ID NO:3 and SEQ ID NO:1); Part 1 is bases 301 to 450 of SEQ ID NO: 3 and bases 1 to 117 of SEQ ID NO: 1. Part 2 is bases 501 to 750 of SEQ ID NO: 3 and bases 118 to 290 of SEQ ID NO: 1. Part 3 is bases 851 to 1050 of SEQ ID NO: 3 and bases 291 to 487 of SEQ ID NO: 1. Part 4 is bases 1151 to 1350 of SEQ ID NO: 3 and bases 488 to 648 of SEQ ID NO: 1. Part 5 is bases 1401 to 1650 of SEQ ID NO: 3 and bases 649 to 841 of SEQ ID NO: 1. Part 6 is bases 1701 to 2140 of SEQ ID NO: 3 and bases 842 to 1197 of SEQ ID NO: 1.

FIG. 8 is the full length promoter of BS92-7 (SEQ ID NO: 5)

FIG. 10 shows an essential region of the BS92-7 promoter (SEQ ID NO: 6).

FIG. 12 is a comparison of BS92-7 sorghum tassel(DNA is SEQ ID NO: 7 and protein is SEQ ID NO: 8)and BS92-7 maize cDNA (DNA is bases 29 to 731 of SEQ ID NO: 1 and protein is residues 10 to 244 of SEQ ID NO: 2).

DISCLOSURE OF THE INVENTION

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated therein are standard methodologies well known to one of ordinary skill in the art. The materials, methods and examples are illustrative only and not limiting.

Genetic male sterility results from a mutation, suppression, or other impact to one of the genes critical to a specific step in microsporogenesis, the term applied to the entire process of pollen formulation. These genes can be collectively referred to as male fertility genes (or, alternatively, male sterility genes). There are many steps in the overall pathway where gene function impacts fertility. This seems aptly supported by the frequency of genetic male sterility in maize. New alleles of male sterility mutants are uncovered in materials that range from elite inbreds to unadapted populations. To date, published genetic male sterility research has been mostly descriptive. Some efforts have been made to establish the mechanism of sterility in maize, but few have been satisfactory. This should not be surprising given the number of genes that have been identified as being responsible for male sterility. One mechanism is unlikely to apply to all mutations.

At U.S. Pat. No. 5,478,369 there is described a method by which a male sterility gene was tagged on maize chromosome 9. Previously, the only described male sterility gene on chromosome 9 was MS2, which has never been cloned and sequenced. See Albertsen, M. and Phillips, R. L., "Developmental Cytology of 13 Genetic Male Sterile Loci in Maize" *Canadian Journal of Genetics & Cytology* 23:195–208 (January 1981). The only fertility gene cloned before that had been the *Arabadopsis* gene described at Aarts, et al., supra.

Figure 1:
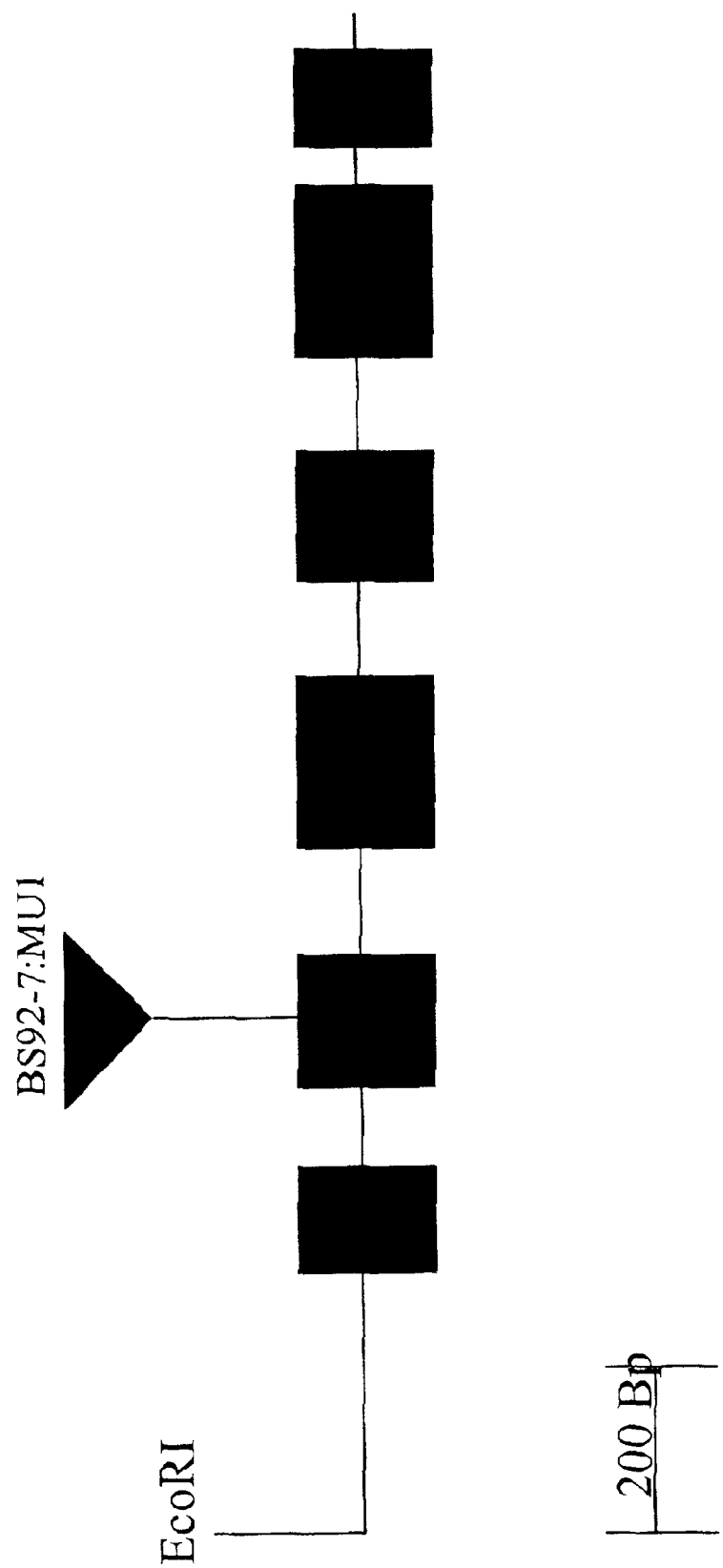
FIG. 1. is a locus map of the male sterility gene BS92-7.

The BS92-7 gene described herein is located on maize chromosome 7 and is critical to male fertility. The locus map is represented at FIG. 1. It can be used in the systems described above, and other systems impacting male fertility.

The maize family cosegregating for sterility was named BS92-7 and was found to have an approximately 7.0 Kb EcoRI fragment that hybridized with a Mu1 probe. A genomic clone from the family was isolated which contained a Mu1 transposon. A probe made from DNA bordering the transposon was found to hybridize to the same ~7.0 Kb EcoRI fragment. This probe was used to isolate cDNA clones from a tassel cDNA library. The cDNA for BS92-7 is 1230 bp, and the Mu insertion occurred in exon 2 of the gene. Expression patterns, as determined by Northern analysis, show tassel specificity with peak expression highest at about the quartet to quartet release stages of microsporogenesis.

Further, it will be evident to one skilled in the art that variations, mutations, derivations including fragments smaller than the entire sequence set forth may be used which retain the male sterility controlling properties of the gene. One of ordinary skill in the art can readily assess the variant or fragment by its introduction into plants homozygous for a stable male sterile allele of BS92-7, followed by observation of the plant's male tissue development.

The invention also includes those nucleotide sequences which selectively hybridize to BS92.7 nucleotide sequences under stringent conditions. In referring to a sequence that "selectively hybridizes" with BS92-7, the term includes reference to hybridization, under stringent hybridization conditions, of a nucleic acid sequence to the specified nucleic acid target sequence to a detectably greater degree (e.g., at least 2-fold over background) than its hybridization to non-target nucleic acid.

The terms "stringent conditions" or "stringent hybridization conditions" includes reference to conditions under which a probe will hybridize to its target sequence, to a detectably greater degree than to other sequences (e.g., at least 2-fold over background). Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

Preferred hybridization conditions for the nucleotide sequence of the invention include hybridization at 42° C. in 50%(w/v) formamide, 6×SSC, 0.5% (w/v) SDS, 100 (g/ml) salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 2×SSC, 0.5% (w/v) SDS, at 65° C. for 30 minutes and repeating. Sequences that correspond to the promoter of the present invention may be obtained using all the above conditions. For purposes of defining the invention, the high stringency conditions are used.

Promoter regions can be readily identified by one skilled in the art. The putative start codon containing the ATG motif is identified and upstream from the start codon is the presumptive promoter. By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements upstream of the TATA box from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as male tissue can be identified, isolated, and used with other core promoters to confirm male tissue-preferred expression.

The isolated promoter sequence of the present invention can be modified to provide for a range of expression levels of the heterologous nucleotide sequence. Less than the entire promoter region can be utilized and the ability to drive anther-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 30 nucleotides of an isolated promoter sequence will be used to drive expression of a nucleotide sequence. It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

Smaller fragments may yet contain the regulatory properties of the promoter so identified and deletion analysis is one method of identifying essential regions. Deletion analysis can occur from both the 5' and 3' ends of the regulatory region. Fragments can be obtained by site-directed mutagenesis, mutagenesis using the polymerase chain reaction and the like. (See, *Directed Mutagenesis: A Practical Approach IRL Press* (1991)). The 3' deletions can delineate the essential region and identify the 3' end so that this region may then be operably linked to a core promoter of choice. Once the essential region is identified, transcription of an exogenous gene may be controlled by the essential region plus a core promoter. The core promoter can be any one of known core promoters such as the Cauliflower Mosaic Virus 35S or 19S promoter (U.S. Pat. No. 5,352,605), ubiquitin promoter (U.S. Pat. No. 5,510,474) the IN2 core promoter (U.S. Pat. No. 5,364,780) or a Figwort Mosaic Virus promoter (Gruber, et al. "Vectors for Plant Transformation" *Methods in Plant Molecular Biology and Biotechnology* Glick et al. eds, CRC Press pp.89–119 (1993)).

The regulatory region of BS92-7 has been identified as including the about 270 base pair region upstream of the putative TATA box. (See FIG. 8.) Further, using the procedures outlined above, it has been determined that an essential region of the promoter includes the −112 to −93 bp upstream of the TATA box.

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al., eds., (1990) *PCR Protocols, A Guide to Methods and Applications*, Academic Press).

Further, the promoter of the present invention can be linked with nucleotide sequences other than the BS92-7 gene to express other heterologous nucleotide sequences. The nucleotide sequence for the promoter of the invention, as well as fragments and variants thereof, can be provided in expression cassettes along with heterologous nucleotide sequences for expression in the plant of interest, more particularly in the male tissue of the plant. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response. Examples of other nucleotide sequences which can be used with the BS92-7 promoter as the exogenous gene of the expression vector include complementary nucleotidic units such as antisense molecules (callase antisense RNA, barnase antisense RNA and chalcone synthase antisense RNA, Ms45 antisense RNA), ribozymes and external guide sequences, an aptamer or single stranded nucleotide sequences. The exogenous nucleotide sequence can also encode auxins, rol B, cytotoxins, diptheria toxin, DAM methylase, avidin, or may be selected from a prokaryotic regulatory system. By way of example, Mariani, et al., *Nature*; Vol. 347; pp. 737; (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Quaas, et al., *Eur. J. Biochem*. Vol. 173: pp. 617 (1988), describe the chemical synthesis of the RNase-T1, while the nucleotide sequence of the barnase gene is disclosed in Hartley, *J. Molec. Biol*.; Vol. 202: pp. 913 (1988). The rolb gene of *Agrobacterium rhizogenes* codes for an enzyme that interferes with auxin metabolism by catalyzing the release of free indoles from indoxyl-β-glucosides. Estruch, et al., *EMBO J*. Vol. 11: pp. 3125 (1991) and Spena, et al., *Theor. Appl. Genet*.; Vol. 84: pp. 520 (1992), have shown that the anther-specific expression of the rolB gene in tobacco resulted in plants having shriveled anthers in which pollen production was severely decreased and demonstrated the rolB gene is another gene that is useful for the control of pollen production. Slightom, et al., *J. Biol. Chem*. Vol. 261: pp. 108 (1985), disclose the nucleotide sequence of the rolB gene. DNA molecules encoding the diphtheria toxin gene can be obtained from the American Type Culture Collection (Rockville, Md.), ATCC No. 39359 or ATCC No. 67011 and see Fabijanski, et al., E. P. Appl. No. 90902754.2, "Molecular Methods of Hybrid Seed Production" for examples and methods of use. The DAM methylase gene is used to cause sterility in the methods discussed at U.S. Pat. Nos. 5,792, 853, 5,689,049 and PCT/US95/15229 Cigan, A. M. and Albertsen, M. C., "Reversible Nuclear Genetic System for Male Sterility in Transgenic Plants". Also see discussion of use of the avidin gene to cause sterility at U.S. Pat. No. 5,962,769.

The invention includes vectors with the BS92-7 gene. A vector is prepared comprising the BS92-7 gene, a promoter that will drive expression of the gene in the plant and a terminator region. As noted, the promoter in the construct may be the native promoter or a substituted promoter which will provide expression in the plant. The choice of promoter will depend upon the use intended of the gene. The promoter in the construct may be an inducible promoter, so that expression of the sense or antisense molecule in the construct can be controlled by exposure to the inducer.

Other components of the vector may be included, also depending upon intended use of the gene. Examples include selectable markers, targeting or regulatory sequences, stabilizing or leader sequences, etc. General descriptions and examples of plant expression vectors and reporter genes can be found in Gruber, et al., "Vectors for Plant Transformation" in *Method in Plant Molecular Biology and Biotechnology*, Glick et al eds;CRC Press pp. 89–119 (1993). The selection of an appropriate expression vector will depend upon the host and the method of introducing the expression vector into the host. The expression cassette can also include at the 3' terminus of the heterologous nucleotide sequence of interest, and a transcriptional and translational termination region functional in plants. The termination region can be native with the promoter nucleotide sequence of the present invention, can be native with the DNA sequence of interest, or can be derived from another source. Convenient termination regions are available from the Ti-plasmid of A. tumefaciens, such as the octopine synthase and nopaline synthase termination regions. See also, Guerineau et al. *Mol. Gen. Genet.* 262:141–144 (1991); Proudfoot *Cell* 64:671–674 (1991); Sanfacon et al. *Genes Dev.* 5:141–149 (1991); Mogen et al. *Plant Cell* 2:1261–1272 (1990); Munroe et al. *Gene* 91:151–158 (1990); Ballas et al. *Nucleic Acids Res.* 17:7891–7903 (1989); Joshi et al. *Nucleic Acid Res.* 15:9627–9639 (1987).

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. *Proc. Nat. Acad. Sci.* USA 86:6126–6130 (1989); potyvirus leaders, for example, TEV leader (Tobacco Etch Virus), Allison et al.; MDMV leader (Maize Dwarf Mosaic Virus), *Virology* 154:9–20 (1986); human immunoglobulin heavy-chain binding protein (BiP), Macejak et al. *Nature* 353:90–94 (1991); untranslated leader from the coat protein mRNA of alfalfa mosaic virus (AMV RNA 4), Jobling et al. *Nature* 325:622–625 (1987); Tobacco mosaic virus leader (TMV), Gallie et al. (1989) *Molecular Biology of RNA*, pages 237–256; and maize chlorotic mottle virus leader (MCMV) Lommel et al. *Virology* 81:382–385 (1991). See also Della-Cioppa et al. *Plant Physiology* 84:965–968 (1987). The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731–3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the promoter sequence of the present invention operably linked to a heterologous nucleotide sequence in an expression cassette can also contain at least one additional nucleotide sequence for a gene to be cotransformed into the organism. Alternatively, the additional sequence(s) can be provided on another transformation vector.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987–992; methotrexate, Herrera Estrella et al. (1983) *Nature* 303:209–213; Meijer et al. (1991) *Plant Mol. Biol.* 16:807–820; hygromycin, Waldron et al. (1985) *Plant Mol. Biol.* 5:103–108; Zhijian et al. (1995) *Plant Science* 108:219–227; streptomycin, Jones et al. (1987) *Mol. Gen. Genet.* 210:86–91; spectinomycin, Bretagne-Sagnard et al. (1996) *Transgenic Res.* 5:131–137; bleomycin, Hille et al. (1990) *Plant Mol. Biol.* 7:171–176; sulfonamide, Guerineau et al. (1990) *Plant Mol. Biol.* 15:127–136; bromoxynil, Stalker et al. (1988) *Science* 242:419–423; glyphosate, Shaw et al. (1986) *Science* 233:478–481; phosphinothricin, DeBlock et al. (1987) *EMBO J.* 6:2513–2518.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, (1992) *Bio/Technology* 10:268; and Weising et al., (1988) *Ann. Rev. Genet.* 22: 421–477. For example, the DNA construct may be introduced into the genomic DNA of the plant cell using techniques such as microprojectile-mediated delivery, Klein et al., (1987) *Nature* 327: 70–73; electroporation, Fromm et al., (1985) *Proc. Natl. Acad. Sci.* 82: 5824; polyethylene glycol (PEG) precipitation, Paszkowski et al., (1984) *EMBO J.* 3: 2717–2722; direct gene transfer WO 85/01856 and EP No. 0 275 069; in vitro protoplast transformation U.S. Pat. No. 4,684,611; and microinjection of plant cell protoplasts or embryogenic callus. Crossway, (1985) *Mol. Gen. Genetics* 202:179–185. Co-cultivation of plant tissue with *Agrobacterium tumefaciens* is another option, where the DNA constructs are placed into a binary vector system. See e.g., U.S. Pat. No. 5,591,616; Ishida et al., (1996) *Nature Biotechnology* 14:745–750. The virulence functions of the *Agrobacterium tumefaciens* host will direct the insertion of the construct into the plant cell DNA when the cell is infected by the bacteria See, for example Horsch et al., (1984) *Science* 233: 496–498, and Fraley et al., (1983) *Proc. Natl. Acad. Sci.* 80: 4803.

Standard methods for transformation of canola are described at Moloney et al. "High Efficiency Transformation of *Brassica napus* using *Agrobacterium* Vectors" *Plant Cell Reports* 8:238–242 (1989). Corn transformation is described by Frornm et al, *Bio/Technology* 8:833 (1990) and Gordon-Kamm et al, supra. *Agrobacterium* is primarily used in dicots, but certain monocots such as maize can be transformed by *Agrobacterium*. See supra and U.S. Pat. No. 5,550,318. Rice transformation is described by Hiei et al., (1992) *The Plant Journal* 6(2): 271–282 (1994, Christou et al, *Trends in Biotechnology* 10:239 and Lee et al, *Proc. Nat'l Acad. Sci.* USA 88:6389 (1991). Wheat can be transformed by techniques similar to those used for transforming corn or rice. Sorghum transformation is described at Casas et al, supra and sorghum by Wan et al, (1994) *Plant Physicol.* 104:37. Soybean transformation is described in a number of publications, including U.S. Pat. No. 5,015,580.

Further detailed description is provided below by way of instruction and illustration and is not intended to limit the scope of the invention.

EXAMPLE 1

Identification and Cosegregation of BS92-7

Figure 2:
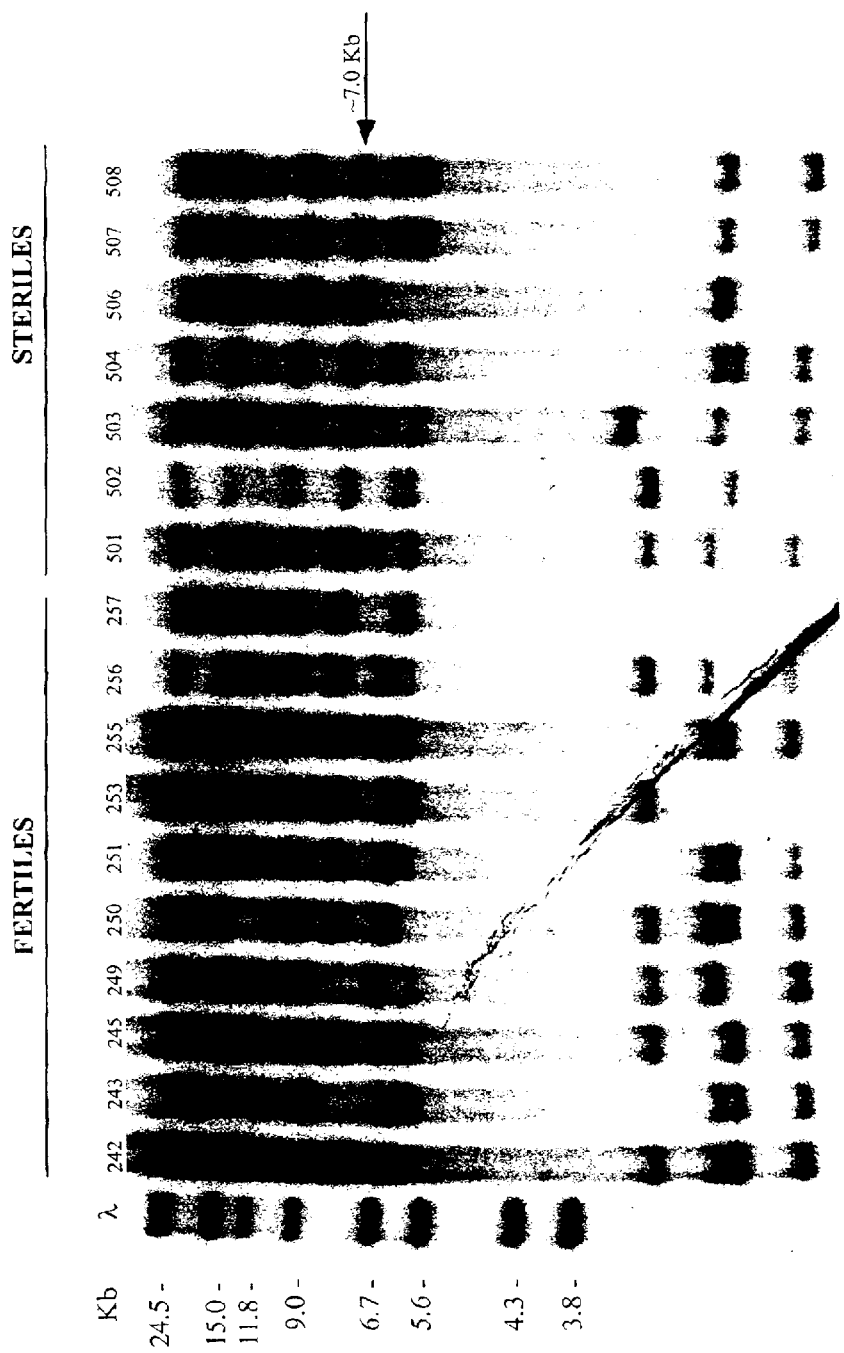
FIG. 2. is a gel of a Southern Blot analysis of EcoRI digested DNA from a Mu family segregating for male sterility and hybridized with a Mu1 probe.

Families of plants from a mutator (Mu) population were identified that segregated for a male sterile phenotype, with none or only a few extruded abnormal anthers, none of which had pollen present. Male sterility is expected to result from those instances where a Mu element has randomly integrated into a gene responsible for some step in microsporogenesis, disrupting its expression. Plants from a segregating $F_2$ family, designated BS92-7, were grown and classified for male fertility/sterility based on the above criteria. Leaf samples were taken and subsequent DNA isolated on approximately 20 plants per phenotypic classification Southern analysis was performed to confirm association of Mu with sterility. Southern analysis is a well known technique to those skilled in the art. This common procedure involves isolating the plant DNA, cutting with restriction endonucleases, fractionating the cut DNA by molecular weight on an agarose gel, and transferring to nylon membranes to fix the separated DNA. These membranes were subsequently hybridized with the Mu-probe fragment that was radioactively labeled with $\alpha^{32}$P-dCTP, and washed in an SDS solution. Southern, E., (1975) "Detection of Specific Sequences Among DNA Fragments by Gel Electrophoresis," *J. Mol. Biol.* 98:503–317. Plants from a segregating $F_2$ BS92-7 family were grown and classified for male fertility/sterility. Leaf sampling and subsequent DNA isolation was accomplished on approximately 20 plants per phenotypic classification. DNA (~7 ug) from 5 fertile and 12 sterile plants was digested with EcoRI and subjected to electrophoresis through a 0.75% agarose gel. The digested DNA was transferred to nylon membrane via Southern transfer. The membrane was hybridized with an internal fragment from the Mu1transposon. Autoradiography of the membrane revealed cosegregation of a 7 Kb EcoRI fragment with the sterility phenotype as shown at FIG. 2. This EcoRI band segregated in the fertile plants suggesting a segregating homozygous-heterozygous wild type condition for the allele.

EXAMPLE 2

Library Construction and Screening

The process of cDNA library screenings is commonly known among those skilled in the art and is described at Sambrook, J., Fritsch, E. F., Maniatis T., et al., (1989) *Molecular Cloning: A Laboratory Manual*, Cold Spring Harbor Laboratory, Cold Spring Harbor Lab Press, Plainview, N.Y. Libraries were created as follows.

DNA from a sterile plant was digested with EcoRI and run on a preparative gel. DNA with a molecular weight between 6.0 and 8.0 kb was excised from the gel, electroeluted and ethanol precipitated. This DNA was ligated into the Lambda Zap vector (Stratagene™) using the manufacturer's protocol. The ligated DNA was packaged into phage particles using Gigapack Gold (Stratagene™). Approximately 500,000 PFU were plated and lifted onto nitrocellulose membranes. Membranes were hybridized with the Mu1probe. A pure clone was obtained after three rounds of screening. The insert was excised from the phage as a plasmid and designated BS927-8.1. A border fragment from this clone was isolated and used to reprobe the original EcoRI cosegregation blot. The 7.0 kb EcoRI fragment is homozygous in all the sterile plants, which confirms that the correct Mu fragment was isolated. Eight of the fertile plants are heterozygous for the 7.0 kb EcoRI band and a 6.2 Kb EcoRI band. Two of the fertile plants are homozygous for the 6.2 kb EcoRI band, presumably the wild type allele.

EXAMPLE 3

Expression Analysis and cDNA Isolation

Figure 3:
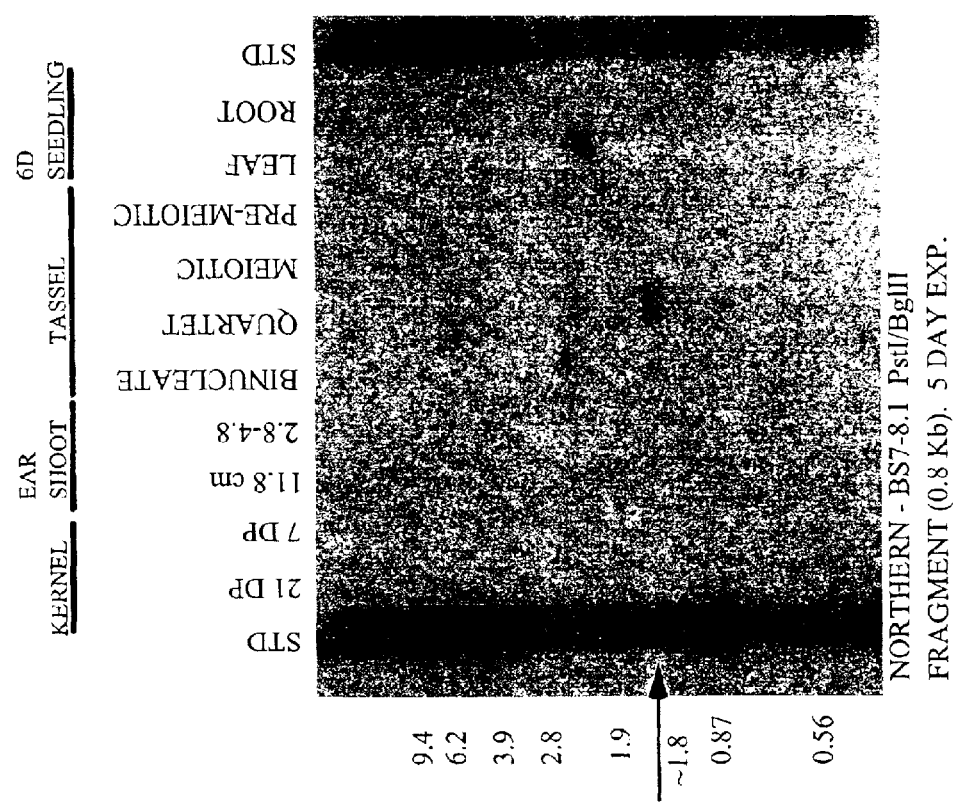
FIG. 3. is a Northern Blot analysis gel of total RNA from various tissues hybridized with a PstI/II BglII fragment from the BS92-7 clone.

Northern analysis can be used to detect expression of genes at various stages of microsporogenesis. Northern analysis is a commonly used technique known to those skilled in the art and is similar to Southern analysis except that mRNA instead of DNA is isolated and placed on the gel. The mRNA is then hybridzed with the labeled probe. Potter, E., et al., (1981) *Proc. Nat. Acad. Sci. USA* 78:6662–6666, Lechelt, et al. (1989) *Mol.Gen.Genet.* 219:225–234. A PstI/BglII fragment from BS927-8.1 was used to probe a northern blot containing kernel, immature ear, seedling and tassel RNA. A signal was seen only in tassel RNA at approximately the quartet stage of microsporogenesis as reflected at FIG. 3. The transcript is about 1.4 kb in length. The same probe was also used to screen a cDNA library constructed from mRNA isolated from meiotic to late uninucleate staged anthers. Two clones, designated BS927-4.1 and BS927-9.1, were isolated from the library.

EXAMPLE 4

Sequence Analysis

Figure 7:
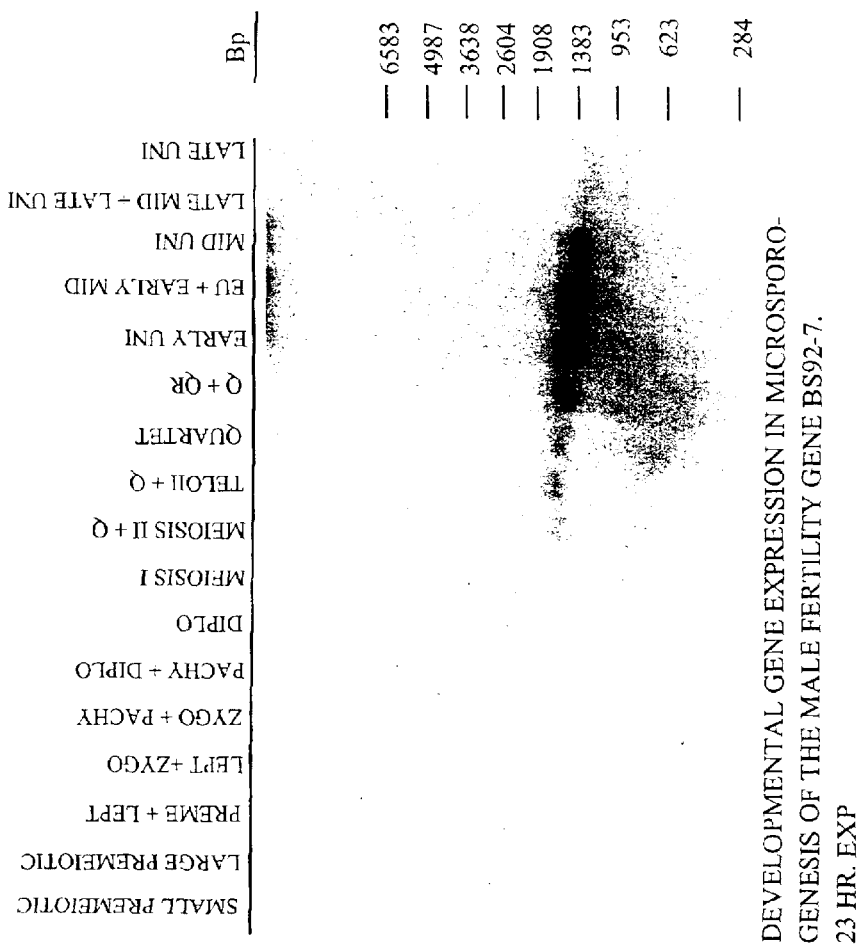
FIG. 7. is a Northern analysis gel showing developmental gene expression in microsporogenesis of the gene BS92-7.

BS927-8.1 genomic clone and the two cDNA clones, BS927-4.1 and BS927-9.1, were sequenced. Sequences methods are well known in the art and this sequencing was accomplished by Loftstrand Labs Limited using the methods discussed at Sanger, F., Nicklen, S., Coulson, A. R. (1977) "DNA Sequences with chain terminating inhibitors" *Proc. Natl. Acad. Sci. USA* 74:5463–5467. The two cDNA clones differ at the 5' end of the molecule. BS927-4.1 contains a TCTC repeat, whereas the BS927-9 does not. When these sequences are compared to the genomic clone, the TCTC repeat is not present and probably represents a cloning artifact in the BS927-4.1 cDNA. The cDNA/genomic comparison reveals six exons and five introns are present in the genomic clone. The cDNA sequence is set forth in FIG. 4 and the genomic shown in FIG. 5. A comparison of the genomic and cDNA is provided in FIG. 6 and demonstrated a 95.95% identity. The Mu1 insertion occurs in exon2. There is a putative Met start codon at position 320 in the genomic clone. Since both cDNAs lack this Met codon, they did not represent full length genes. Subsequent cDNA screening with BS927-4.1 allowed for the isolation of clone BS927-11.1. This clone was only sequenced at the 5' end to determine its start point. It was determined that BS927-11.1 lacks 2 bases of the Met codon (ATG) and is the longest cDNA isolated. Further expression studies were done using the BS927-4.1 cDNA probe against a Northern containing mRNA at discrete stages of microsporogenesis. Signal is detected from meiosis II/quartet to mid-uninucleate, with maximal signal being at quartet to quartet release as shown at FIG. 7.

EXAMPLE 5

Identification of Promoter and its Essential Regions

Comparison of the BS927-8.1 genomic clone with the cDNA clones BS927-1.11, BS927-4.1 and BS927-9.1 allowed identification of introns and exons in BS927. This in turn permitted identification of ORFs, one of which extended through most of the cDNA sequence, and was most likely the protein coding sequence of the BS927 gene. Testing for codon preference and non-randomness in the third position of each codon confirmed that this was the likely protein-coding ORF. At the amino acid level, the protein that would be encoded has 52% similarity (42% identity) with the maize gene Al, which encodes dihydroflavanol reductase and is required for synthesis of anthocyanins and phlobaphenes.

Regulatory regions of anther genes, such as promoters, may be identified in genomic subclones using functional analysis, usually verified by the observation of reporter gene expression in anther tissue and a lower level or absence of reporter gene expression in non-anther tissue. The possibility of the regulatory regions residing "upstream" or 5' ward of the transcriptional start site can be tested by subcloning a DNA fragment that contains the upstream region into expression vectors for transient expression experiments. It is expected that smaller subgenomic fragments may contain the regions essential for male-tissue preferred expression. For example, the essential regions of the CaMV 19S and 35S promoters have been identified in relatively small fragments derived from larger genomic pieces as described in U.S. Pat. No. 5,352,605.

The selection of an appropriate expression vector with which to test for functional expression will depend upon the host and the method of introducing the expression vector into the host and such methods are well known to one skilled in the art. For eukaryotes, the regions in the vector include regions that control initiation of transcription and control processing. These regions are operably linked to a reporter gene such as UidA, encoding β-glucuronidase (GUS), or luciferase. General descriptions and examples of plant expression vectors and reporter genes can be found in Gruber, et al., supra. GUS expression vectors and GUS gene cassettes are commercially available from Clonetech, Palo Alto, Calif., while luciferase expression vectors and luciferase gene cassettes are available from Promega Corporation, Madison, Wis. Ti plasmids and other *Argrobacterium* vectors are described in Ishida, Y., et al., (1996) *Nature Biotechnology*; Vol. 14; pp. 745–750; and in U.S. Pat. No. 5,591,616.

Expression vectors containing putative regulatory regions located in genomic fragments can be introduced into intact tissues such as staged anthers, embryos or into callus. Methods of DNA delivery include microprojectile bombardment, DNA injection, electroporation and *Agrobacterium*-mediated gene transfer (see Gruber, et al., supra, U.S. Pat. No. 5,591,616, and Ishida, Y., et al., supra). General methods of culturing plant tissues are found in Gruber, et al., supra.

For the transient assay system, staged, isolated anthers are immediately placed onto tassel culture medium (Pareddy, D. R. and J. F. Petelino, (1989) *Crop Sci. J.*; Vol. 29; pp. 1564–1566;) solidified with 0.5% Phytagel (Sigma, St. Louis) or other solidifying media. The expression vector DNA is introduced within 5 hours preferably by microprojectile-mediated delivery with 1.2 μm particles at 1000–1100 Psi. After DNA delivery, the anthers are incubated at 26° C. upon the same tassel culture medium for 17 hours and analyzed by preparing a whole tissue homogenate and assaying for GUS or for lucifierase activity (see Gruber, et al., supra).

Upstream of the likely translational start codon of BS927, only 319 bp of BS927 DNA were present in the genomic clone BS927-8.1. Translational fusions via an engineered NcoI site were generated with reporter genes encoding luciferase and β-glucuronidase to test whether this fragment of DNA had promoter activity in transient expression assays of bombarded plant tissues. Activity was demonstrated in anthers and not in coleoptiles, roots and calli, suggesting anther-preferred or anther-specific promoter activity.

A reasonable TATA box was observed by inspection upstream of the translational start codon. The genomic clone BS927-8.1 thus includes only about 266 bp upstream of the putative TATA box. For typical plant genes, the start of transcription is 26–36 bp downstream of the TATA box, which would give the BS927 mRNA a 5'-nontranslated leader of only about 17–27 nucleotides (nt). The total BS927 subgenomic fragment of only 319 bp, including nontranslated leader, start of transcription, TATA box and sequences upstream of the TATA box, was thus shown to be sufficient for promoter activity. See FIG. 8, which is SEQ. ID NO.5. It will be appreciated by those skilled in the art that promoter fusions with genes, open reading frames, RNA-encoding sequences and the like may be either at or close to the native start of transcription or at the start of translation or downstream of the start codon. The putative TATA box (TTTATAA) is underlined. Thus, the present invention encompasses a DNA molecule having a nucleotide sequence of SEQ ID NO. 5 (or those with sequence identity or which hybridize thereto) and having the function of a male tissue-preferred regulatory region.

Deletion analysis can occur from both the 5' and 3' ends of the regulatory region: fragments can be obtained by site-directed mutagenesis, mutagenesis using the polymerase chain reaction, and the like (*Directed Mutagenesis: A Practical Approach*; IRL Press; (1991)). The 3' end of the male tissue-preferred regulatory region can be delineated by proximity to the putative TATA box or by 3' deletions if necessary. The essential region may then be operably linked to a core promoter of choice via cloning restriction sites introduced into the region immediately upstream of the TATA box or as defined by 3' deletion analysis. Once the essential region is identified, transcription of an exogenous gene may be controlled by the male tissue-preferred region of BS92-7 plus a core promoter. The core promoter can be any one of known core promoters such as a Cauliflower Mosaic Virus 35S or 19S promoter (U.S. Pat. No. 5,352, 605), ubiquitin (U.S. Pat. No. 5,510,474), the IN2 core promoter (U.S. Pat. No. 5,364,780), or a Figwort Mosaic Virus promoter (Gruber, et al., supra). Preferably, the promoter is the core promoter of a male tissue-preferred gene or the CaMV 35S core promoter. More preferably, the promoter is from a male tissue-preferred gene and in particular, the BS92-7 core promoter.

Further mutational analysis, for example by linker scanning, a method well-known to the art, can identify small segments containing sequences required for anther-preferred expression. These mutations may introduce modifications of functionality such as in the levels of expression, in the timing of expression or in the tissue of expression. Mutations may also be silent and have no observable effect.

The foregoing procedures were used to identify essential regions of the BS92-7 promoter. After linking the promoter with the luciferase marker gene, mutational analyses were performed. The 319 bp promoter/nontranslated leader region of the genomic clone BS7 comprises 266 bp upstream of the putative TATA box. Deletion of the upstream-most one half (approximately) of this upstream region to an MluI site reduced transient promoter activity about tenfold in anthers, although activity was not eliminated. Introduction of a BglII site at −15 to −10 relative to the putative TATA box did not greatly affect activity, but the combination of this cloning site modification with the deletion eliminated activity.

Figure 9:
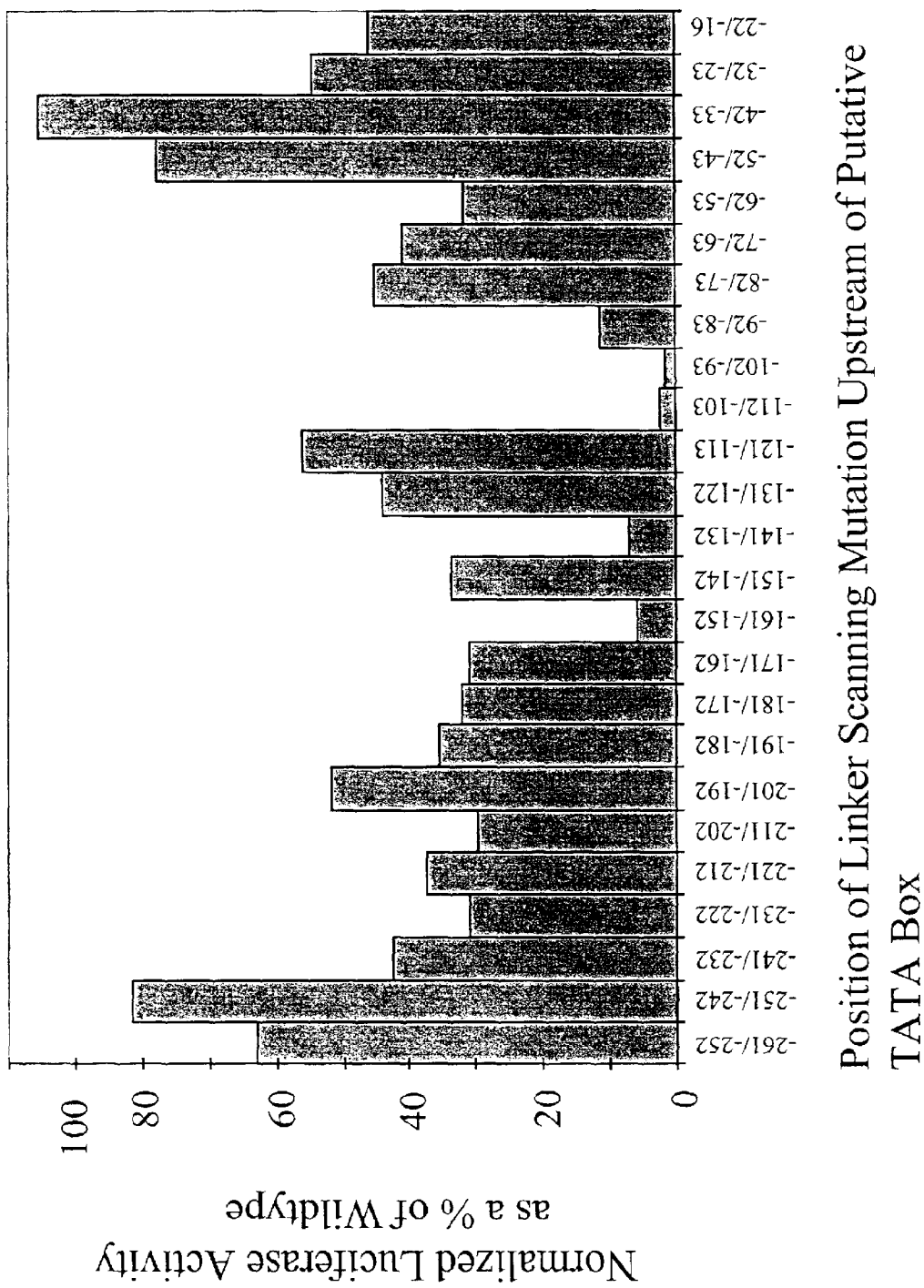
FIG. 9. is a bar graph showing luciferase activity after substitution by restriction site linker scanning of select small (9–10 bp) regions of the BS92-7 essential promoter fragment.

Linker scanning was initiated from −261 through −16 relative to the putative TATA box, mostly in 10 bp increments, as represented in FIG. 9. The bar graph shows each 7–10 bp substituted segment on the x-axis. The y-axis shows the normalized luciferase activity as a percent of wild type promoter activity. The linker scanning constructs and wild type control included the BglII cloning site. The minimal promoter is further represented in FIG. 10. The TATA box is identified by underlining. A single critical region from −112 through −93 relative to the putative TATA box was observed, with additional regions having a significant impact located at −161 to −152; −141 to −132; and −92 to −83 relative to the putative TATA box. The region from about −102 to −93 relative to the putative TATA box includes two overlapping copies of a sequence, the P motif, implicated in the function of other anther promoter upstream regions as well as promoters activated by the maize P gene product. The myb-homologous P gene controls phlobaphene pigmentation in maize floral organs by directly activating a flavonoid biosynthetic gene subset. (Grotewald, E., B. J. Drummond, B. Bowen, and T. Peterson (1994) *Cell* 76:543–553.)

EXAMPLE 6

BS92-7 Promoter used to Drive MS45 Gene

Figure 11:
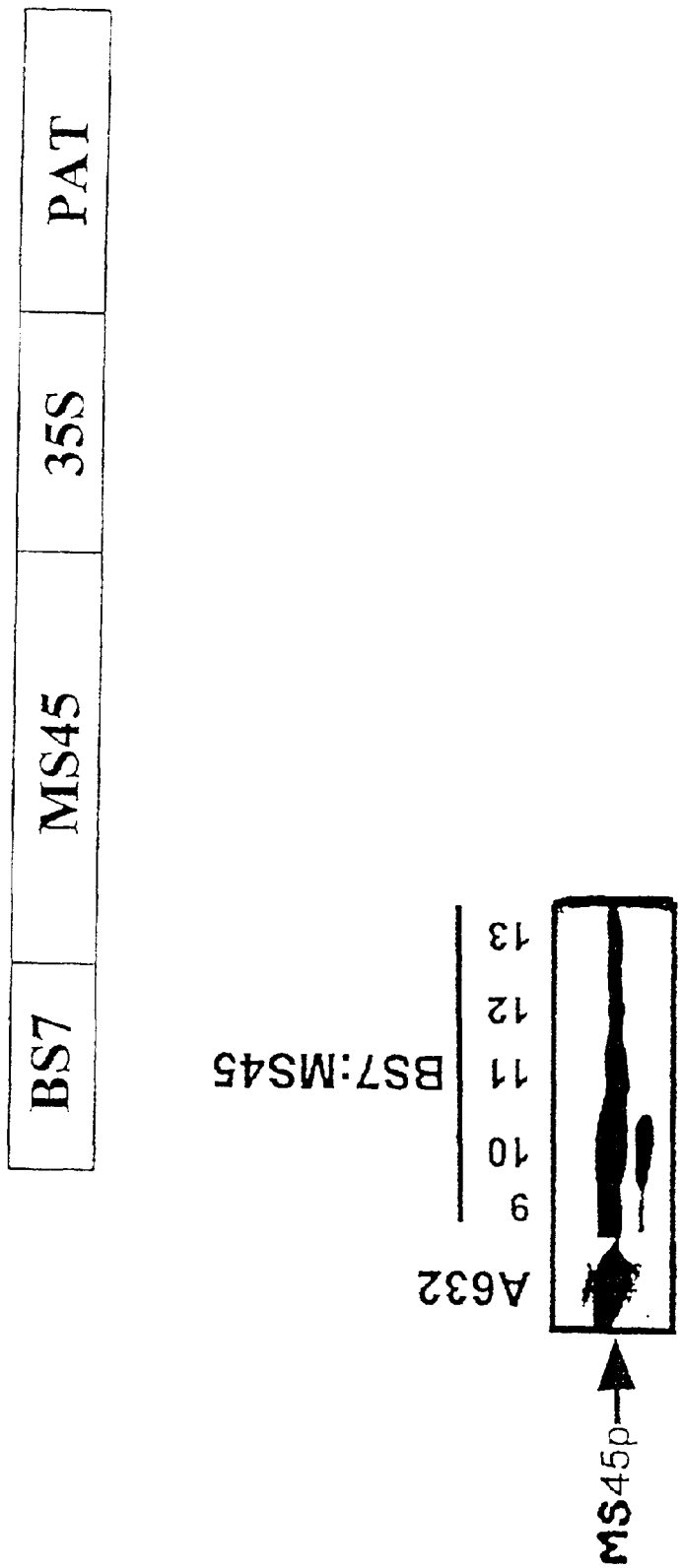
FIG. 11 shows a diagram of a construct used to express the MS45 male fertility gene using the BS7 promoter, and an immunoblot analysis of the MS45 protein from maize plants transformed with the construct.

The MS45 gene is a male fertility gene in maize and mutations in the gene result in breakdown of microsporogenesis during vacuolation of the microspores rendering the plants male sterile. When the cloned maize MS45 gene is introduced into such mutated male sterile plants, the gene can complement the mutation and confer male fertility. For a complete discussion of the MS45 gene and its promoter, see U.S. Pat. Nos. 5,478,369 and 6,037,523, incorporated herein by reference. PHP6641 is a pUC8 plasmid containing the MS45 gene promoter and coding region including introns, nucleotides 1–3335 cloned as NcoI DNA fragment upstream of the 35S::PAT selectable marker gene as described above. Site directed mutagenesis (as per Su T. S. and El-Gewely M. R. supra, was used to introduce a NcoI restriction enzyme recognition site at the translation start codon of the MS45 gene (nucleotide 1389). A 4.7 kp HindIII-EcoRI DNA fragment containing the mutagenized version of MS45–35S::PAT was cloned in plasmid pSB11 (pSB31 from Ishida et al supra.) lacking the EcoRI DNA fragment insert carrying the 35S GUS and 35SBAR genes resulting in PHP10890. To produce PHP12025, the BS92.7 promoter replaced the MS45 promoter. This was then introduced into a construct, shown in FIG. 11. This construct was introduced by *Agrobacterium*-mediated transformation as described above into a mutant maize plant which was male sterile as a result of a mutation of the MS45 gene. All 22 events generated from the transformation were restored to a male-fertile phenotype. Immunoblot analysis of the MS45 protein from the plants is also shown in FIG. 11. MS45 protein from an inbred expressing wild-type MS45 gene served as the control. Protein extracts were isolated from anthers staged at tetrad release to early vacuolate stages of microspore development. The MS45 protein was expressed to nearly wild-type levels when transcribed from the maize BS92.7 promoter. Thus the BS92.7 promoter was able to drive appropriate expression of a gene required to restore fertility to a male-sterile mutant line. Table 1 summarizes the results below.

TABLE 1

| Construct | Description | % Male-Fertile | % Male-Sterile | Number of events |
|---|---|---|---|---|
| PHP10890 | MS45::MS45 | 100% | | 11 |
| PHP12205 | BS92.7::MS45 | 100% | | 22 |

EXAMPLE 7

Impacting Male Fertility Using the BS7 Promoter

In addition, the BS92.7 promoter was able to drive expression of a cytotoxic gene to confer male sterility on a male-fertile genotype. The constructs to produce male sterile plants were developed as follows. The *E. coli* DNA adenine methylase gene (DAM gene) as described at U.S. Pat. No. 5,792,853, was used. MS45:DAM-35SPAT(PHP12634)

The DAM gene was modified by site-directed mutagenesis (Su and El-Gewley, (1988) *Gene* 69:81–89) and a SmaI site introduced at nucleotide 186, nine nucleotides 5' to the initiating codon ATG of the DAM gene. The NcoI site of a 1.4 kb HindIII-NcoI fragment containing the maize MS45 promoter found on plasmid PHP6054 was filled-in with dNTPs usingT4 DNA polymerase and ligated to the SmaI site contained at the 5' end of the DAM gene. Transcription of this gene was terminated by the addition of the 3' sequences from the potato proteinase inhibitor II gene (PinII) (nucleotides 2–310; An et al., (1989) *Plant Cell* 1:115–122).

To construct the maize transformation vector PHP12634 (MS45::DAM-35SPAT), the 2.5 kb chimeric gene containing the MS45 promoter, the DAM gene and PinII 3' non-translated region was cloned as a HindIII-NcoI fragment upstream of the 35S::PAT gene in the vector pSB11 (pSB31from Ishida et al., supra, lacking the EcoRI fragment insert carrying the 35SGUS and 35SBAR genes). The PAT gene encodes the enzyme phosphinothricin acetyltransferase (PAT) from *Streptomyces viridochomagenes* (nucleotides 6 to 557). See, EP 0 275 957 A; Genbank accession number A02774. It was placed under the transcriptional regulation of the cauliflower mosaic virus (CAMV) 35S promoter and terminator regions (nucleotides 6906 to 7439, and 7439–7632). See U.S. Pat. No. 5,352,605 and Franck et al., (1980) *Cell* 21:285–294. The 35S::PAT component was contained on an NcoI-KpnI fragment as described in the expression cassette pDH51 (Pietrzak et al., (1986) *Nucleic Acids Res.* 14:5857–5868).

PHP12635 (BS7:DAM/35S:PAT) was constructed by replacing the MS45 promoter in PHP12634 with the BS7 promoter.

In the following experiment the BS92.7 promoter was used to direct the transcription of the sterility gene, Dam-methylase (DAM). A construct using the MS45 promoter for transcription of DAM was also transformed into wild-type maize. Table 2 below reflects that 100% of the events containing BS92.7::DAM were male sterile, compared to the MS45::DAM construct in which only 25% of the events were male sterile.

TABLE 2

| Construct | Description | % Male-Fertile | % Male-Sterile | Number of events |
| --- | --- | --- | --- | --- |
| PHP12634 | MS45::DAM | 75% | 25% | 24 |
| PHP12635 | BS92.7::DAM | 0 | 100% | 10 |

EXAMPLE 8

Allelism

The BS927-8.1 clone was mapped in an ECB RFLP population using EcoRI as the enzyme. The clone maps on the long arm of chromosome 7 between the molecular markers bnl15.40 and umc110a. The male sterile mutant, ms7, is the only known male sterile that maps to chromosome 7. Allelism crosses were initiated with the BS92-7 mutant and the ms7 stock. Progeny from this cross segregated for male sterility indicating that the same gene is responsible for the mutant phenotypes in both the BS92-7 and ms7 families.

EXAMPLE 9 ms7 Isolation

Clone ms7-5.1 was purified and sequenced using internal primers already constructed for the BS92-7 sequencing work. There is one extra Ser residue in the ms7 deduced protein as compared to the BS92-7. The major difference between the two is a 33 bp deletion in the promoter region of ms7. Transient assays of the ms7 promoter fragment show that it is active in anthers.

As noted above, the BS92-7 nucleotide sequence is allelic to the known maize male sterile mutation ms7. When BS92-7 is mutated, male sterility will result. It may be introduced into plants to impact male sterility.

EXAMPLE 10

BS92-7 Sorghum Tassel RT-PCR and BS92-7 Maize cDNA Comparison

A homologue of BS92-7 was identified in sorghum. The sorghum-BS92-7 cDNA was isolated by using the maize BS92-7 gene primers in a polymerase chain reaction with sorghum flower cDNA as the template. The resultant cDNA fragment was sequenced by methods described supra and then compared to the BS92-7 cDNA from maize. Nucleotide sequence comparisons are set forth in FIG. 12, which shows 89.1% identity between the nucleotide sequences and 94% identity between the predicted protein sequences.

As is evident from the above, the BS92-7 gene is critical to male fertility in plants.

Thus it can be seen that the invention achieves at least all of its objectives.

What is claimed is:

1. An isolated nucleic acid sequence comprising SEQ ID NO: 5.

2. An isolated male tissue-preferred regulatory region comprising SEQ ID NO: 6.

* * * * *

SEQUENCE LISTING

<160> NUMBER OF SEQ ID NOS: 8

<210> SEQ ID NO 1
<211> LENGTH: 1197
<212> TYPE: DNA
<213> ORGANISM: Zea mays
<220> FEATURE:
<221> NAME/KEY: CDS
<222> LOCATION: (2)..(991)

<400> SEQUENCE: 1

```
g gtg acc tca agc aag ggc aag gta tgc gta acc ggg gcc tca ggc ttt      49
  Val Thr Ser Ser Lys Gly Lys Val Cys Val Thr Gly Ala Ser Gly Phe
    1               5                  10                  15 gtt gcc tct tgg ctt atc aaa cgg ctc ctc gag tct gga tat cat gtg        97
Val Ala Ser Trp Leu Ile Lys Arg Leu Leu Glu Ser Gly Tyr His Val
             20                  25                  30 gta ggg act gtc agg gac cca gga aat cac caa aaa aca gcc cac ctt       145
Val Gly Thr Val Arg Asp Pro Gly Asn His Gln Lys Thr Ala His Leu
         35                  40                  45 tgg aaa tta cct ggc gct aaa gag agg ctg caa atc gtg cga gct aat       193
Trp Lys Leu Pro Gly Ala Lys Glu Arg Leu Gln Ile Val Arg Ala Asn
     50                  55                  60
```

-continued

| | |
|---|---|
| ctg ttg gaa gaa ggg agc ttc gac agc gcc gtg atg gcc tgt gag ggt<br>Leu Leu Glu Glu Gly Ser Phe Asp Ser Ala Val Met Ala Cys Glu Gly<br>65                                 70                        75                     80 | 241 |
| gta ttc cac act gca tcc ccc gtc ctc gct aaa ccc gac tct act agc<br>Val Phe His Thr Ala Ser Pro Val Leu Ala Lys Pro Asp Ser Thr Ser<br>                       85                        90                     95 | 289 |
| aag gag gac acg ctc gtc cct gcg gtg aac ggt act ctg aac gtg ctg<br>Lys Glu Asp Thr Leu Val Pro Ala Val Asn Gly Thr Leu Asn Val Leu<br>               100                     105                   110 | 337 |
| aga tcg tgc aag aag aac ccc ttc ctg aaa agg gtc gtc ctt acg tct<br>Arg Ser Cys Lys Lys Asn Pro Phe Leu Lys Arg Val Val Leu Thr Ser<br>         115                     120                   125 | 385 |
| tcg tcg tct gcg gtg agg atc agg gac gac ggt ggc cag tcc agt aac<br>Ser Ser Ser Ala Val Arg Ile Arg Asp Asp Gly Gly Gln Ser Ser Asn<br>130                               135                    140 | 433 |
| atc tcg ctg gac gaa acg aca tgg agc tcc gtg cca ctc tgc gag aag<br>Ile Ser Leu Asp Glu Thr Thr Trp Ser Ser Val Pro Leu Cys Glu Lys<br>145                               150                   155                   160 | 481 |
| atg cat cta tgg tat gcc cta gcc aag gta ttt gca gag aaa gcg gcg<br>Met His Leu Trp Tyr Ala Leu Ala Lys Val Phe Ala Glu Lys Ala Ala<br>                     165                     170                   175 | 529 |
| tgg gag ttc gcc aag gag aac ggc atc gac ctt gtg act gtc ctc ccg<br>Trp Glu Phe Ala Lys Glu Asn Gly Ile Asp Leu Val Thr Val Leu Pro<br>               180                     185                   190 | 577 |
| tcg ttc gtg atc ggg ccc agt ttg tcc cac gag cta tgc gtt acc gct<br>Ser Phe Val Ile Gly Pro Ser Leu Ser His Glu Leu Cys Val Thr Ala<br>         195                     200                   205 | 625 |
| tca gac gtc cta ggc cta ttc caa ggc gac acg gca agg ttc agc tcg<br>Ser Asp Val Leu Gly Leu Phe Gln Gly Asp Thr Ala Arg Phe Ser Ser<br>210                               215                    220 | 673 |
| tac gga aga atg ggg tac gtc cac atc gac gac gtt gcg agc agc cac<br>Tyr Gly Arg Met Gly Tyr Val His Ile Asp Asp Val Ala Ser Ser His<br>225                               230                    235                   240 | 721 |
| atc ctg gtg tac gag gtc ccc cag gcc gcc ggg agg tac ctg tgc agc<br>Ile Leu Val Tyr Glu Val Pro Gln Ala Ala Gly Arg Tyr Leu Cys Ser<br>               245                     250                   255 | 769 |
| tca gtg gtg ctg gac aac gac gag ctg gtc tcc tcg ctc gcg aaa cgc<br>Ser Val Val Leu Asp Asn Asp Glu Leu Val Ser Ser Leu Ala Lys Arg<br>                     260                     265                   270 | 817 |
| tac ccg ata ttc ccc ata ccc cgg agg ctg aac agc ccc tac ggc aag<br>Tyr Pro Ile Phe Pro Ile Pro Arg Arg Leu Asn Ser Pro Tyr Gly Lys<br>         275                     280                   285 | 865 |
| cag tcg tac cag ctg aac acg tcg aag ctg cag ggg ctg ggc ttc aag<br>Gln Ser Tyr Gln Leu Asn Thr Ser Lys Leu Gln Gly Leu Gly Phe Lys<br>290                               295                    300 | 913 |
| ttc aga ggg gtg cag gag atg ttc gac gac tgc gtg cag tcg ctc aaa<br>Phe Arg Gly Val Gln Glu Met Phe Asp Asp Cys Val Gln Ser Leu Lys<br>305                               310                    315                 320 | 961 |
| gac cag ggc cac ctg ctg gag tgc ccc ctg tgaactgcga tggggtgcc<br>Asp Gln Gly His Leu Leu Glu Cys Pro Leu<br>               325                     330 | 1011 |
| tcctgtgaac gcccgttttt tttttcttc aataattcca cgtcatgtca cggtgtcctc | 1071 |
| gcgcagactg ctactgtcag gtgtcagggc gtcatagctc acgggctcta cggctacatg | 1131 |
| aataaaatgt cacgctagct cgtcatttgc tttgccattt aaaaaaaaaa aaaaaaaaaa | 1191 |
| ctcgag | 1197 |

<210> SEQ ID NO 2
<211> LENGTH: 330

<212> TYPE: PRT
<213> ORGANISM: Zea mays

<400> SEQUENCE: 2

```
Val Thr Ser Ser Lys Gly Lys Val Cys Val Thr Gly Ala Ser Gly Phe
1               5                   10                  15

Val Ala Ser Trp Leu Ile Lys Arg Leu Leu Glu Ser Gly Tyr His Val
            20                  25                  30

Val Gly Thr Val Arg Asp Pro Gly Asn His Gln Lys Thr Ala His Leu
        35                  40                  45

Trp Lys Leu Pro Gly Ala Lys Glu Arg Leu Gln Ile Val Arg Ala Asn
    50                  55                  60

Leu Leu Glu Glu Gly Ser Phe Asp Ser Ala Val Met Ala Cys Glu Gly
65                  70                  75                  80

Val Phe His Thr Ala Ser Pro Val Leu Ala Lys Pro Asp Ser Thr Ser
                85                  90                  95

Lys Glu Asp Thr Leu Val Pro Ala Val Asn Gly Thr Leu Asn Val Leu
            100                 105                 110

Arg Ser Cys Lys Lys Asn Pro Phe Leu Lys Arg Val Val Leu Thr Ser
        115                 120                 125

Ser Ser Ser Ala Val Arg Ile Arg Asp Asp Gly Gly Gln Ser Ser Asn
    130                 135                 140

Ile Ser Leu Asp Glu Thr Thr Trp Ser Ser Val Pro Leu Cys Glu Lys
145                 150                 155                 160

Met His Leu Trp Tyr Ala Leu Ala Lys Val Phe Ala Glu Lys Ala Ala
                165                 170                 175

Trp Glu Phe Ala Lys Glu Asn Gly Ile Asp Leu Val Thr Val Leu Pro
            180                 185                 190

Ser Phe Val Ile Gly Pro Ser Leu Ser His Glu Leu Cys Val Thr Ala
        195                 200                 205

Ser Asp Val Leu Gly Leu Phe Gln Gly Asp Thr Ala Arg Phe Ser Ser
    210                 215                 220

Tyr Gly Arg Met Gly Tyr Val His Ile Asp Asp Val Ala Ser Ser His
225                 230                 235                 240

Ile Leu Val Tyr Glu Val Pro Gln Ala Ala Gly Arg Tyr Leu Cys Ser
                245                 250                 255

Ser Val Val Leu Asp Asn Asp Glu Leu Val Ser Ser Leu Ala Lys Arg
            260                 265                 270

Tyr Pro Ile Phe Pro Ile Pro Arg Arg Leu Asn Ser Pro Tyr Gly Lys
        275                 280                 285

Gln Ser Tyr Gln Leu Asn Thr Ser Lys Leu Gln Gly Leu Gly Phe Lys
    290                 295                 300

Phe Arg Gly Val Gln Glu Met Phe Asp Asp Cys Val Gln Ser Leu Lys
305                 310                 315                 320

Asp Gln Gly His Leu Leu Glu Cys Pro Leu
                325                 330
```

<210> SEQ ID NO 3
<211> LENGTH: 2544
<212> TYPE: DNA
<213> ORGANISM: Zea mays

<400> SEQUENCE: 3

```
gaattctcgt ctcggcggtc aactgaaccg taaacagtgg aaagtggata ctctttctct   60
ctctgcaatc cgtgccgtgg aagcaaatgg cgcagtcgcc tacttatcac accaacttat  120
```

```
cacctagaaa agcgacgcgt cctggatcga ttgcaaatct acctccaacc aacccagctt    180
tgtatctgct tactgtgatc accaaagttg tgctgatacg atgtgcgatt attgctcttt    240
cttctctaga atgttcctgc cgatgcttta aagagaagg ttggtcagca tcgatctctg    300
ccagtgtcta gctgagaaca tggtgacctc aagcaagggc aaggtatgcg taaccggggc    360
ctcaggcttt gttgcctctt ggcttatcaa acggctcctc gagtctggat atcatgtggt    420
agggactgtc agggacccag gtatttgcga aatatcatta ctatcgtatc agtcctcttt    480
attacattaa taattcttga ttaccaattt tttctttttt tttttggta acccacaagg    540
aaatcaccaa aagacagccc acctttggaa attacctggc gctaaagaga ggctgcaaat    600
cgtgcgagct gatctgttgg aagaagggag cttcgacagc gccgtgatgg cctgtgaggg    660
tgtattccac actgcatccc ccgtcctcgc taaacccgac tctactagca aggcatgcca    720
tcgccgcata tatatgca tatctggacc atgcatccta ctgcagcctt ttctatacgg    780
aagcgcgttg catctaccgt acgtgaagct agctatctaa gctaagctgt ttttcatgca    840
tgcatggtgc aggaggacac gctcgtccct gcggtgaacg gtactctgaa cgtgctgaga    900
tcgtgcaaga agaacccgtt cctgaaaagg gtcgtcctta cgtcttcgtc gtctgcggtg    960
aggatcaggg acgacggtgg ccagtccagt aacatctcgc tggacgaaac gacatggagc    1020
tccgtgccac tctgcgagaa gatgcatgtg agatactact gaacagtgtc tactctctct    1080
ctctctgtca tcgatctcaa accgtgatct gaaaaacacg catgcgcgca cacgttgccg    1140
tcgtcgtccc ttttgttgtt cacccgaagc tatggtatgc cctagccaag gtatttgcag    1200
agaaagcggc gtgggagttc gccaaggaga acggcatcga ccttgtgact gtcctcccgt    1260
cgttcgtgat cgggcccagt ttgtcccacg aactatgcgt taccgcttca gacgtcctag    1320
gcctattcca aggtattcat ctcaatcatt grbcgtacgt gttctggttt tcgtatgtta    1380
aatagatgac tggaaacaag aggtatacat atatatactc tctgttcctc ctccccccc    1440
cccccaccc ccaggcgaca cggcaaggtt cagctcgtac ggaagaatgg ggtacgtcca    1500
catcgacgac gttgcgagca gccacatcct ggtgtacgag gcccccaggg ccgccgggag    1560
gtacctgtgc agctcagtgg tgctggacaa cgacgagctg gtctcctcgc tcgcgaaacg    1620
ctacccgata ttccccatac cccggaggtc agtcgtcgtc gcgtcgtctg gatgtgcgtg    1680
ccattttaag atctctgaac gggagagccg tgtgcatggt ccgttctgct gcaggctgaa    1740
cagcccctac ggcaagcagt cgtaccagct gaacacgtcg aagctgcagg ggctgggctt    1800
caagttcaga ggggtgcagg agatgttcga cgactgcgta cagtcgctca aagaccaggg    1860
acacctgctg gagtgccccc tgtgaactgc gatggggtgc ctccgcctgt gaacgcgccg    1920
gttgggttgc gtcccgaacc cgctgttaat tcgttttttt ttcttcaata attccacgtc    1980
atgtcacggt gtcctcgcgc agactgctac tgtcagggcg tcatagctca cgggctctcc    2040
ggctacatga ataaaaatgt cacgctcgtc atttgctttg cctttttttt tgggttcgtt    2100
ctgcgaactt ccgttcgctg tgtgtacttg tggctgccgg tcgccttgtc ggtgtggcga    2160
ctgatgatgg tgatcggagg caggcaccgg tgtgtgcgtg cgatcaaccg aacgccatgt    2220
ggcggttggg atggacgaat ggctccacca tcgatctgag tcattcggat tttgaaccgc    2280
tgatttgtcc actggacggc actagcatca agattcagtc tcaaatccca aattcctcaa    2340
cgcaaagcca caaagagaga atgaatgtac agtgtttcaa gccacagctc actagctcaa    2400
aagtagtgag catgcacacc tgtatttaca tgcatgcatg tacacccca cccccactac    2460
```

```
ttgtacactt tgtaaaccaa ccaaccaacc aaccaagcaa gcaatcaagc aaacacacag    2520
agcaaaccgt acgtggctgg cgcc                                           2544

<210> SEQ ID NO 4
<211> LENGTH:
<212> TYPE:
<213> ORGANISM:

<400> SEQUENCE: 4

000

<210> SEQ ID NO 5
<211> LENGTH: 322
<212> TYPE: DNA
<213> ORGANISM: Zea mays

<400> SEQUENCE: 5
gaattctcgt ctcggcggtc aactgaaccg taaacagtgg aaagtggata ctctttctct     60
ctctgcaatc cgtgccgtgg aagcaaatgg cgcagtcgcc tacttatcac accaacttat    120
cacctagaaa agcgacgcgt cctggatcga ttgcaaatct acctccaacc aacccagctt    180
tgtatctgct tactgtgatc accaaagttg tgctgatacg atgtgcgatt attgctcttt    240
cttctctaga atgttcctgc cgatgcttta agagaagg ttggtcagca tcgatctctg       300
ccagtgtcta gctgagaaca tg                                             322

<210> SEQ ID NO 6
<211> LENGTH: 187
<212> TYPE: DNA
<213> ORGANISM: Zea mays

<400> SEQUENCE: 6
cgcgtcctgg atcgattgca aatctacctc caaccaaccc agctttgtat ctgcttactg     60
tgatcaccaa agttgtgctg atacgatgtg cgattattgc tctttcttct ctagaatgtt   120
cctgccgatg ctttataaga gaaggttggt cagcatcgat ctctgccagt gtctagctga   180
gaacatg                                                              187

<210> SEQ ID NO 7
<211> LENGTH: 697
<212> TYPE: DNA
<213> ORGANISM: Sorghum sp.
<220> FEATURE:
<221> NAME/KEY: CDS
<222> LOCATION: (1)..(696)

<400> SEQUENCE: 7 gta acc ggg gct tca ggc ttt att gcc tct tgg ctt atc aaa cgg ctg       48
Val Thr Gly Ala Ser Gly Phe Ile Ala Ser Trp Leu Ile Lys Arg Leu
 1               5                  10                  15 ctc gag tct gga tat cat gtg gta ggg act gtc aga gac cca gga aat       96
Leu Glu Ser Gly Tyr His Val Val Gly Thr Val Arg Asp Pro Gly Asn
             20                  25                  30 cac caa aaa aca gca cac ctt tgg aaa tta cct ggt gcc aaa gag agg      144
His Gln Lys Thr Ala His Leu Trp Lys Leu Pro Gly Ala Lys Glu Arg
         35                  40                  45 ctg caa att gtg cga gct gat ctg ttg gaa gaa ggg agc ttt gac aat      192
Leu Gln Ile Val Arg Ala Asp Leu Leu Glu Glu Gly Ser Phe Asp Asn
     50                  55                  60
```

```
gct gtc atg gac tgt gat ggc gtc ttc cac act gca tcc cct gtg ctc        240
Ala Val Met Asp Cys Asp Gly Val Phe His Thr Ala Ser Pro Val Leu
65              70                  75                  80 gct aaa tct gat tct agt agc aag gag gaa acg ctt tgt cca gca gta        288
Ala Lys Ser Asp Ser Ser Ser Lys Glu Glu Thr Leu Cys Pro Ala Val
            85                  90                  95 aac ggt act ctg aat gtg cta aga tcg tgc aag aag aac cca ttt ctg        336
Asn Gly Thr Leu Asn Val Leu Arg Ser Cys Lys Lys Asn Pro Phe Leu
        100                 105                 110 aaa agg gtt gtt ctt acg tct tca tca tct gca gtg agg att agg gat        384
Lys Arg Val Val Leu Thr Ser Ser Ser Ala Val Arg Ile Arg Asp
                115                 120                 125 gat gat cag cct aat atc tca ctg gat gaa aca aca tgg agc tct gtg        432
Asp Asp Gln Pro Asn Ile Ser Leu Asp Glu Thr Thr Trp Ser Ser Val
130                 135                 140 cca ctc tgt gaa aag atg cag cta tgg tat gcc cta gcg aag gta ttt        480
Pro Leu Cys Glu Lys Met Gln Leu Trp Tyr Ala Leu Ala Lys Val Phe
145                 150                 155                 160 gca gag aaa gcg gca tgg gaa ttc gcc aag gag aac aac atc gac ctt        528
Ala Glu Lys Ala Ala Trp Glu Phe Ala Lys Glu Asn Asn Ile Asp Leu
                165                 170                 175 gtg act gtc ctc cca tca ttt gtg atc ggg ccc agt tta tcc cat gaa        576
Val Thr Val Leu Pro Ser Phe Val Ile Gly Pro Ser Leu Ser His Glu
            180                 185                 190 cta tgt gtt acc gct tca gat gtc cta ggc tta ttc caa ggt gac acg        624
Leu Cys Val Thr Ala Ser Asp Val Leu Gly Leu Phe Gln Gly Asp Thr
        195                 200                 205 gca agg ttc agt tct tac gga aga atg gga tac gtt cac atc gac gat        672
Ala Arg Phe Ser Ser Tyr Gly Arg Met Gly Tyr Val His Ile Asp Asp
    210                 215                 220 gtt gcg acc agc cac atc ctg gtg t                                      697
Val Ala Thr Ser His Ile Leu Val
225                 230

<210> SEQ ID NO 8
<211> LENGTH: 232
<212> TYPE: PRT
<213> ORGANISM: Sorghum sp.

<400> SEQUENCE: 8

Val Thr Gly Ala Ser Gly Phe Ile Ala Ser Trp Leu Ile Lys Arg Leu
1               5                   10                  15

Leu Glu Ser Gly Tyr His Val Val Gly Thr Val Arg Asp Pro Gly Asn
                20                  25                  30

His Gln Lys Thr Ala His Leu Trp Lys Leu Pro Gly Ala Lys Glu Arg
            35                  40                  45

Leu Gln Ile Val Arg Ala Asp Leu Leu Glu Glu Gly Ser Phe Asp Asn
        50                  55                  60

Ala Val Met Asp Cys Asp Gly Val Phe His Thr Ala Ser Pro Val Leu
65              70                  75                  80

Ala Lys Ser Asp Ser Ser Ser Lys Glu Glu Thr Leu Cys Pro Ala Val
                85                  90                  95

Asn Gly Thr Leu Asn Val Leu Arg Ser Cys Lys Lys Asn Pro Phe Leu
            100                 105                 110

Lys Arg Val Val Leu Thr Ser Ser Ser Ala Val Arg Ile Arg Asp
        115                 120                 125

Asp Asp Gln Pro Asn Ile Ser Leu Asp Glu Thr Thr Trp Ser Ser Val
130                 135                 140
```

```
                                -continued

Pro Leu Cys Glu Lys Met Gln Leu Trp Tyr Ala Leu Ala Lys Val Phe
145                 150                 155                 160

Ala Glu Lys Ala Ala Trp Glu Phe Ala Lys Glu Asn Asn Ile Asp Leu
                165                 170                 175

Val Thr Val Leu Pro Ser Phe Val Ile Gly Pro Ser Leu Ser His Glu
            180                 185                 190

Leu Cys Val Thr Ala Ser Asp Val Leu Gly Leu Phe Gln Gly Asp Thr
        195                 200                 205

Ala Arg Phe Ser Ser Tyr Gly Arg Met Gly Tyr Val His Ile Asp Asp
    210                 215                 220

Val Ala Thr Ser His Ile Leu Val
225                 230
```